United States Patent
Justin et al.

(10) Patent No.: US 8,864,797 B2
(45) Date of Patent: Oct. 21, 2014

(54) SYSTEMS AND METHODS FOR INTRA-OPERATIVE TENSION AND FIXATION OF ZIPKNOT ACL FIXATION

(75) Inventors: Daniel F. Justin, Orlando, FL (US); Andrew Fauth, River Heights, UT (US); Joshua A. Butters, Chandler, AZ (US); Chad Lewis, Layton, UT (US); Karen E. Mohr, Salt Lake City, UT (US); Carlyle Creger, Wellsville, UT (US); Nicholas Slater, Chandler, AZ (US); Mark J. Mooradian, Phoenix, AZ (US); Greta Jo Hays, Logan, UT (US); M. Mary Sinnott, Logan, UT (US); Jeremy D. Borchert, Austin, TX (US); Stuart Goble, Logan, UT (US)

(73) Assignee: Coorstek Medical LLC, Providence, UT (US)

( * ) Notice: Subject to any disclaimer, the term of this patent is extended or adjusted under 35 U.S.C. 154(b) by 0 days.

(21) Appl. No.: 13/243,715

(22) Filed: Sep. 23, 2011

(65) Prior Publication Data

US 2012/0065731 A1    Mar. 15, 2012

Related U.S. Application Data

(63) Continuation-in-part of application No. 12/828,856, filed on Jul. 1, 2010, now abandoned.

(60) Provisional application No. 61/222,574, filed on Jul. 2, 2009, provisional application No. 61/333,363, filed on May 11, 2010, provisional application No. 61/333,548, filed on May 11, 2010, provisional application No. 61/386,396, filed on Sep. 24, 2010.

(51) Int. Cl.
*A61B 17/04* (2006.01)
*A61F 2/08* (2006.01)

(52) U.S. Cl.
CPC .......... *A61F 2/0811* (2013.01); *A61B 17/0487* (2013.01); *A61B 2017/0404* (2013.01); *A61F 2002/0852* (2013.01); *A61F 2002/0882* (2013.01); *A61B 2017/0477* (2013.01); *A61B 2017/0459* (2013.01)
USPC ........................................ 606/232; 623/13.14

(58) Field of Classification Search
USPC ............. 623/13.11–13.14; 606/232, 233, 228
See application file for complete search history.

(56) References Cited

U.S. PATENT DOCUMENTS

| 65,499 A | * | 6/1867 | Miller | ......................... 24/115 R |
| 757,820 A | | 4/1904 | Lyke | |

(Continued)

FOREIGN PATENT DOCUMENTS

| WO | WO2006029127 | 3/2006 |
| WO | WO2009009617 | 1/2009 |
| WO | WO2009049002 | 4/2009 |

*Primary Examiner* — Alvin Stewart
(74) *Attorney, Agent, or Firm* — Maywood IP Law; G. Jo Hays; David W. Meibos

(57) ABSTRACT

A line lock system may include a line routed through a plate. The plate may have an elongated body with a plurality of passageways. The line is routed to form at least one one-way slide so no knots are required. The system may include filaments routed through the passageways of the plate or around a dogbone feature of the plate. The filaments may be used to toggle the plate after passage through a hole to prevent withdrawal of the plate back through the hole. The system may include a line lock stabilizer or counter-tension tool to stabilize the line lock as the line is adjusted. The system may include a compression limiter to selectively reduce compression in the one-way slide to facilitate adjustment of the line. The line lock stabilizer, counter-tension tool, or compression limiter may be a filament.

39 Claims, 30 Drawing Sheets

(56) References Cited

U.S. PATENT DOCUMENTS

| | | | |
|---|---|---|---|
| 1,713,106 A | 5/1929 | Ulfers | |
| 1,806,162 A * | 5/1931 | Hahn | 24/712.6 |
| 3,168,850 A * | 2/1965 | Tennican | 411/342 |
| 3,332,118 A * | 7/1967 | Temple et al. | 403/353 |
| 3,399,432 A * | 9/1968 | Merser | 24/114.7 |
| 3,699,969 A * | 10/1972 | Allen | 606/187 |
| 3,880,166 A | 4/1975 | Fogarty | |
| 4,439,079 A * | 3/1984 | Losada | 411/345 |
| 4,721,103 A * | 1/1988 | Freedland | 606/319 |
| 4,723,634 A | 2/1988 | Fisk | |
| 4,790,850 A | 12/1988 | Dunn | |
| 4,910,834 A | 3/1990 | Minkler | |
| 4,946,377 A | 8/1990 | Kovach | |
| 5,098,433 A * | 3/1992 | Freedland | 606/63 |
| 5,306,301 A * | 4/1994 | Graf et al. | 606/232 |
| 5,454,821 A * | 10/1995 | Harm et al. | 606/148 |
| 5,562,668 A * | 10/1996 | Johnson | 623/13.13 |
| 5,645,588 A | 7/1997 | Sklar | |
| 5,693,060 A | 12/1997 | Martin | |
| 5,769,894 A * | 6/1998 | Ferragamo | 606/148 |
| 5,800,543 A | 9/1998 | McLeod | |
| 6,010,525 A * | 1/2000 | Bonutti et al. | 606/232 |
| 6,030,007 A | 2/2000 | Bassily | |
| 6,045,574 A * | 4/2000 | Thal | 606/232 |
| 6,068,648 A * | 5/2000 | Cole et al. | 606/232 |
| 6,095,282 A * | 8/2000 | Sadeck | 182/6 |
| 6,139,565 A * | 10/2000 | Stone et al. | 606/232 |
| 6,161,999 A * | 12/2000 | Kaye et al. | 411/344 |
| 6,193,754 B1 * | 2/2001 | Seedhom | 623/13.11 |
| 6,287,065 B1 * | 9/2001 | Berlin | 411/340 |
| 6,440,134 B1 * | 8/2002 | Zaccherotti et al. | 606/62 |
| 6,451,030 B2 * | 9/2002 | Li et al. | 606/139 |
| 6,511,498 B1 * | 1/2003 | Fumex | 606/232 |
| 6,517,578 B2 * | 2/2003 | Hein | 623/13.13 |
| 6,533,802 B2 * | 3/2003 | Bojarski et al. | 606/232 |
| 6,569,186 B1 * | 5/2003 | Winters et al. | 606/232 |
| 6,599,319 B2 | 7/2003 | Knudsen | |
| 6,645,227 B2 * | 11/2003 | Fallin et al. | 606/232 |
| 6,652,563 B2 * | 11/2003 | Dreyfuss | 606/232 |
| 6,682,549 B2 * | 1/2004 | Bartlett | 606/232 |
| 6,689,154 B2 * | 2/2004 | Bartlett | 606/232 |
| 6,773,436 B2 * | 8/2004 | Donnelly et al. | 606/232 |
| 6,902,573 B2 * | 6/2005 | Strobel et al. | 606/232 |
| 6,923,823 B1 * | 8/2005 | Bartlett et al. | 606/232 |
| 6,972,027 B2 * | 12/2005 | Fallin et al. | 606/232 |
| 6,994,725 B1 * | 2/2006 | Goble | 623/13.14 |
| 7,087,073 B2 * | 8/2006 | Bonutti | 606/232 |
| 7,097,654 B1 * | 8/2006 | Freedland | 606/232 |
| 7,150,757 B2 * | 12/2006 | Fallin et al. | 606/232 |
| 7,500,983 B1 * | 3/2009 | Kaiser et al. | 606/232 |
| 7,530,990 B2 * | 5/2009 | Perriello et al. | 606/232 |
| 7,556,640 B2 * | 7/2009 | Foerster | 606/326 |
| 7,566,339 B2 * | 7/2009 | Fallin et al. | 606/232 |
| 7,572,275 B2 * | 8/2009 | Fallin et al. | 606/232 |
| 7,594,923 B2 * | 9/2009 | Fallin et al. | 606/232 |
| 7,615,061 B2 * | 11/2009 | White et al. | 606/148 |
| 7,637,926 B2 * | 12/2009 | Foerster et al. | 606/232 |
| 7,641,672 B2 * | 1/2010 | Fallin et al. | 606/232 |
| 7,641,694 B1 | 1/2010 | Goble | |
| 7,651,509 B2 * | 1/2010 | Bojarski et al. | 606/139 |
| 7,695,503 B1 * | 4/2010 | Kaiser et al. | 606/300 |
| 7,722,644 B2 * | 5/2010 | Fallin et al. | 606/232 |
| 7,736,108 B1 * | 6/2010 | Bruce et al. | 411/346 |
| 7,776,077 B2 * | 8/2010 | Kaiser et al. | 606/300 |
| 7,806,909 B2 | 10/2010 | Fallin | |
| 7,819,898 B2 * | 10/2010 | Stone et al. | 606/232 |
| 7,846,180 B2 * | 12/2010 | Cerier | 606/232 |
| 7,857,830 B2 * | 12/2010 | Stone et al. | 606/232 |
| 7,867,253 B2 * | 1/2011 | McMichael et al. | 606/232 |
| 7,875,057 B2 * | 1/2011 | Cook et al. | 606/232 |
| 7,875,058 B2 * | 1/2011 | Holmes, Jr. | 606/232 |
| 7,887,551 B2 * | 2/2011 | Bojarski et al. | 606/139 |
| 7,934,506 B2 * | 5/2011 | Woodson et al. | 128/860 |
| 7,938,847 B2 * | 5/2011 | Fanton et al. | 606/232 |
| 8,052,719 B2 * | 11/2011 | Paulos | 606/232 |
| 8,057,511 B2 * | 11/2011 | Flores et al. | 606/232 |
| 8,109,965 B2 * | 2/2012 | Stone et al. | 606/232 |
| 8,162,997 B2 * | 4/2012 | Struhl | 606/300 |
| 8,221,454 B2 * | 7/2012 | Schaffhausen | 606/232 |
| 8,221,455 B2 * | 7/2012 | Shurnas et al. | 606/232 |
| 8,221,463 B2 * | 7/2012 | Zucherman et al. | 606/249 |
| 8,231,674 B2 * | 7/2012 | Albertorio et al. | 623/13.14 |
| 8,308,780 B2 * | 11/2012 | Kaiser et al. | 606/300 |
| 8,439,976 B2 * | 5/2013 | Albertorio et al. | 623/13.14 |
| 2001/0014825 A1 * | 8/2001 | Burke et al. | 623/13.14 |
| 2002/0019634 A1 * | 2/2002 | Bonutti | 606/60 |
| 2002/0128684 A1 * | 9/2002 | Foerster | 606/232 |
| 2004/0002734 A1 * | 1/2004 | Fallin et al. | 606/232 |
| 2004/0153153 A1 * | 8/2004 | Elson et al. | 623/13.14 |
| 2004/0254593 A1 | 12/2004 | Fallin | |
| 2005/0277961 A1 | 12/2005 | Walters | |
| 2006/0282081 A1 | 12/2006 | Fanton | |
| 2006/0293709 A1 * | 12/2006 | Bojarski et al. | 606/232 |
| 2007/0162125 A1 | 7/2007 | Mahoney | |
| 2008/0046009 A1 | 2/2008 | Schaneville | |
| 2008/0161852 A1 * | 7/2008 | Kaiser et al. | 606/232 |
| 2008/0177302 A1 * | 7/2008 | Shurnas | 606/228 |
| 2008/0287991 A1 | 11/2008 | Fromm | |
| 2009/0143821 A1 | 6/2009 | Stupak | |
| 2009/0182335 A1 * | 7/2009 | Struhl | 606/60 |
| 2010/0204731 A1 | 8/2010 | Hart | |
| 2010/0312341 A1 * | 12/2010 | Kaiser et al. | 623/13.14 |
| 2011/0022061 A1 * | 1/2011 | Orphanos et al. | 606/139 |
| 2011/0125189 A1 * | 5/2011 | Stoll et al. | 606/232 |
| 2011/0160856 A1 * | 6/2011 | Sinnott et al. | 623/13.14 |
| 2011/0301619 A1 * | 12/2011 | Walters | 606/144 |
| 2011/0301708 A1 * | 12/2011 | Stone et al. | 623/13.14 |
| 2012/0046747 A1 * | 2/2012 | Justin et al. | 623/13.14 |
| 2012/0053630 A1 * | 3/2012 | Denham et al. | 606/232 |
| 2012/0059416 A1 * | 3/2012 | Justin et al. | 606/232 |
| 2012/0065677 A1 * | 3/2012 | West, Jr. | 606/232 |
| 2012/0065678 A1 * | 3/2012 | James | 606/232 |
| 2012/0065731 A1 * | 3/2012 | Justin et al. | 623/13.14 |
| 2012/0078299 A1 * | 3/2012 | Ramos Clamote | 606/232 |
| 2012/0116452 A1 * | 5/2012 | Stone et al. | 606/232 |
| 2012/0123474 A1 * | 5/2012 | Zajac et al. | 606/232 |
| 2012/0123541 A1 * | 5/2012 | Albertorio et al. | 623/13.14 |
| 2012/0245630 A1 * | 9/2012 | Napolitano et al. | 606/232 |
| 2012/0290002 A1 * | 11/2012 | Astorino | 606/232 |
| 2013/0035720 A1 * | 2/2013 | Perriello et al. | 606/232 |
| 2013/0053884 A1 * | 2/2013 | Roorda | 606/232 |
| 2013/0079822 A1 * | 3/2013 | Maiorino et al. | 606/232 |
| 2013/0103085 A1 * | 4/2013 | Hart et al. | 606/232 |
| 2013/0197577 A1 * | 8/2013 | Wolf et al. | 606/232 |
| 2013/0197580 A1 * | 8/2013 | Perriello et al. | 606/232 |
| 2013/0218205 A1 * | 8/2013 | Cleon | 606/232 |

\* cited by examiner

SYSTEMS AND METHODS FOR INTRA-OPERATIVE TENSION AND FIXATION OF ZIPKNOT ACL FIXATION

CROSS-REFERENCE TO RELATED APPLICATIONS

This application is a continuation-in-part of:

U.S. patent application Ser. No. 12/828,856 filed 1 Jul. 2010, and is entitled SYSTEMS AND METHODS FOR ZIP KNOT ACL FIXATION, which claims the benefit of the following:

U.S. Provisional Patent Application No. 61/222,574 filed 2 Jul. 2009, and is entitled ZIP KNOT ACL FIXATION BUTTON;

U.S. Provisional Patent Application No. 61/333,363 filed 11 May 2010, and is entitled ZIP KNOT ACL FIXATION BUTTON; and U.S. Provisional Patent Application No. 61/333,548 filed 11 May 2010, and is entitled ZIP KNOT ACL FIXATION BUTTON.

This application also claims the benefit of:

U.S. Provisional Patent Application No. 61/386,396 filed 24 Sep. 2010, and is entitled INTRA-OPERATE TENSION AND FIXATION OF AN ACL GRAFT.

The above documents are hereby incorporated by reference in their entirety.

The following documents are also hereby incorporated by reference in their entirety:

U.S. patent application Ser. No. 11/001,866 filed 1 Dec. 2004, now U.S. Pat. No. 7,594,923, and is entitled LINE LOCK SUTURE ATTACHMENT SYSTEMS AND METHODS;

U.S. patent application Ser. No. 10/936,376 filed 7 Sep. 2004, now U.S. Pat. No. 7,566,339, and is entitled ADJUSTABLE LINE LOCKS AND METHODS;

U.S. patent application Ser. No. 10/459,375 filed 11 Jun. 2003, now U.S. Pat. No. 7,150,757, and is entitled ADJUSTABLE LINE LOCKS AND METHODS;

U.S. patent application Ser. No. 11/112,814 filed 21 Apr. 2005, now U.S. Pat. No. 7,641,694, and is entitled LINE LOCK GRAFT RETENTION SYSTEM AND METHOD;

U.S. patent application Ser. No. 11/125,885 filed 8 May 2005, now U.S. Pat. No. 7,722,644, and is entitled COMPACT LINE LOCKS AND METHODS; and U.S. patent application Ser. No. 11/142,933 filed 2 Jun. 2005, now abandoned, and is entitled BONE IMPLANTS WITH INTEGRATED LINE LOCKS.

BACKGROUND OF THE INVENTION

1. The Field of the Invention

The present disclosure relates generally to anterior cruciate ligament (ACL) repair and the fixation of an ACL graft on the cortical side of the bone. The technology disclosed herein may also be used for other suspensory fixation applications such as bone/tendon or bone/ligament attachment.

2. The Relevant Technology

Currently ACL repair requires cortical fixation using some type of fixation device that can retain a graft ligament passed through a bone tunnel while maintaining fixation on the cortical side of the bone. Currently there are buttons on the market that allow for fixation without passing through the bone tunnel. Knots tied on, around or through the button are used to hold the graft and the button in place. However, knots are known for reducing the strength of the fixation.

In addition, knots do not offer the amount of tension typically desired by physicians because in tying the knot tension is often relinquished in order to achieve a completed knot. Numerous devices have been developed to eliminate the need to tie knots as a way of securing a line. The devices that accomplish the same function as a knot, which is in part to secure a line to retain tension in a portion of the line, are typically referred to as line locks. These line locks can be used as a one-way directional slide to increase tension in a line without relinquishing that tension to tie a knot.

Current ACL repair systems will engage a graft and then fix the graft using knots tied to a body on the cortical side of the bone. Physicians either have to fix the graft using cord or line prior to passage through the bone tunnel and then readjust the tension, or pass the lines and cords through the bone tunnel without tension and then adjust the tension after pass through, again, tying knots to fix the graft to the cortical fixation device.

In addition currently physicians must choose a proper suture length and bight length of a sling to hold the graft. In this case the surgeon must have multiple sutures with multiple bight lengths available in the operating room (OR) and if the improper length is chosen first then the surgeon will be required to find a different suture length and bight length leading to more guess work and longer surgery times.

As the above described techniques illustrate, the existing systems and procedures for ACL repair may not be as effective as desired.

SUMMARY OF THE INVENTION

In an aspect of the disclosed technology, a system includes a line with a locking portion and a standing portion. The locking portion has a constricted section and a compression section. The system also includes a line lock with a body at least partially bounding a plurality of passageways and a line lock stabilizer. The locking portion of the line is routed through at least some of the passageways so that the constricted section is between the line lock and the compression section and a length of the standing portion extends from the line lock. The line lock stabilizer stabilizes the line lock while the length of the standing portion is adjusted.

In an embodiment, the standing portion couples the system to a structure.

In other embodiments, the standing portion is looped around the structure or encircles the structure.

In yet other embodiments, the standing portion is embedded within the structure, inserted through an anchor embedded in the structure, passed through the structure, or positioned behind the structure.

In yet another embodiment, the length of the standing portion is adjusted to remove slack between the line lock and the structure.

In yet another embodiment, the structure is selected from the group consisting of a soft tissue, a muscle, a cartilage, a cartilage graft, a fascia, a tendon, a ligament, a ligament graft, an anterior cruciate ligament graft, a hard tissue, a bone, an autograft, an allograft, a xenograft, and a synthetic graft.

In yet another embodiment, the line lock stabilizer resists tension in the line tending to adjust the length of the standing portion.

In yet other embodiments, the line lock stabilizer pushes or pulls on the line lock to resist tension in the line tending to adjust the length of the standing portion.

In yet other embodiments, the line lock stabilizer pushes or pulls the line lock against a support.

In yet another embodiment, the line lock stabilizer is coupled to the line lock.

In yet another embodiment, the system includes a key and keyhole connection between the line lock stabilizer and the line lock.

In yet another embodiment, the line lock stabilizer is routed through at least one of the passageways.

In yet another embodiment, the line lock stabilizer is a shaft.

In yet another embodiment, the shaft has a through hole.

In yet another embodiment, the line lock stabilizer is a filament.

In yet another embodiment, the constricted section is compressed between the compression section and the line lock in response to tension in the line tending to lengthen the standing portion so that the system resists lengthening of the standing portion.

In yet another embodiment, the line has a working portion. The locking portion is between the working portion and the standing portion. The length of the standing portion is adjusted by pulling on the working portion.

In yet another embodiment, the line has a second locking portion. The standing portion is between the locking portion and the second locking portion. The second locking portion is coupled to the line lock.

In yet another embodiment, the second locking portion has a second constricted section and a second compression section. The second locking portion is routed through at least some of the passageways so that the second constricted section is between the line lock and the second compression section.

In yet another embodiment, the line has a first working portion and a second working portion. The locking portion is between the first working portion and the standing portion. The second locking portion is between the second working portion and the standing portion. The length of the standing portion is adjusted by pulling on at least one of the first and second working portions.

In another aspect of the disclosed technology, another system includes a line with a locking portion and a standing portion. The locking portion has a constricted section and a compression section. The system also includes a line lock with a body at least partially bounding a plurality of passageways and a counter-tension tool. The locking portion of the line is routed through at least some of the passageways so that the constricted section is between the line lock and the compression section and a length of the standing portion extends from the line lock. The counter-tension tool stabilizes the line lock against tension in the line tending to draw the line through the line lock.

In an embodiment, the standing portion couples the system to a structure.

In other embodiments, the standing portion is looped around the structure or encircles the structure.

In yet other embodiments, the standing portion is embedded within the structure, inserted through an anchor embedded in the structure, passed through the structure, or positioned behind the structure.

In yet another embodiment, the length of the standing portion is adjusted to remove slack between the line lock and the structure.

In yet another embodiment, the structure is selected from the group consisting of a soft tissue, a muscle, a cartilage, a cartilage graft, a fascia, a tendon, a ligament, a ligament graft, an anterior cruciate ligament graft, a hard tissue, a bone, an autograft, an allograft, a xenograft, and a synthetic graft.

In yet another embodiment, the counter-tension tool resists tension in the line tending to draw the line through the line lock.

In yet other embodiments, the counter-tension tool pushes or pulls on the line lock to resist tension in the line tending to draw the line through the line lock.

In yet other embodiments, the counter-tension tool pushes or pulls the line lock against a support.

In yet another embodiment, the counter-tension tool is coupled to the line lock.

In yet another embodiment, the system includes a key and keyhole connection between the counter-tension tool and the line lock.

In yet another embodiment, the counter-tension tool is routed through at least one of the passageways.

In yet another embodiment, the counter-tension tool is a shaft.

In yet another embodiment, the shaft has a through hole.

In yet another embodiment, the counter-tension tool is a filament.

In yet another embodiment, the constricted section is compressed between the compression section and the line lock in response to tension in the line tending to lengthen the standing portion so that the system resists lengthening of the standing portion.

In yet another embodiment, the line has a working portion. The locking portion is between the working portion and the standing portion. The line is drawn through the line lock by pulling on the working portion.

In yet another embodiment, the line has a second locking portion. The standing portion is between the locking portion and the second locking portion. The second locking portion is coupled to the line lock.

In yet another embodiment, the second locking portion has a second constricted section and a second compression section. The second locking portion is routed through at least some of the passageways so that the second constricted section is between the line lock and the second compression section.

In yet another embodiment, the line has a first working portion and a second working portion. The locking portion is between the first working portion and the standing portion. The second locking portion is between the second working portion and the standing portion. The line is drawn through the line lock by pulling on at least one of the first and second working portions.

In yet another aspect of the disclosed technology, yet another system includes a line with a working portion, a locking portion, and a standing portion. The locking portion is between the working portion and the standing portion. The locking portion has a constricted section and a compression section. The system also includes a line lock with a body at least partially bounding a plurality of passageways. The locking portion of the line is routed through at least some of the passageways so that the constricted section is between the line lock and the compression section, a length of the working portion extends from the line lock, and a length of the standing portion extends from the line lock. A tension on the line tending to lengthen the working portion is aligned with a tension on the line tending to lengthen the standing portion.

In an embodiment, the standing portion couples the system to a structure.

In other embodiments, the standing portion is looped around the structure, encircles the structure, or passes through the structure.

In yet other embodiments, the standing portion is embedded within the structure, inserted through an anchor embedded in the structure, or positioned behind the structure.

In yet another embodiment, the length of the standing portion is adjusted to remove slack between the line lock and the structure.

In yet another embodiment, the structure is selected from the group consisting of a soft tissue, a muscle, a cartilage, a cartilage graft, a fascia, a tendon, a ligament, a ligament graft, an anterior cruciate ligament graft, a hard tissue, a bone, an autograft, an allograft, a xenograft, and a synthetic graft.

In yet other embodiments, the working portion and the standing portion extend from opposite sides of the line lock or from the same side of the line lock.

In yet another embodiment, the line lock includes a member coupled to the body. The member is transverse to at least one of the tension tending to lengthen the working portion and the tension tending to lengthen the standing portion.

In yet another embodiment, the member is movable relative to at least one of the tension tending to lengthen the working portion and the tension tending to lengthen the standing portion. A range of motion of the member relative to at least one of the tension tending to lengthen the working portion and the tension tending to lengthen the standing portion includes a position in which the member is transverse to at least one of the tension tending to lengthen the working portion and the tension tending to lengthen the standing portion.

In yet another embodiment, the range of motion of the member relative to at least one of the tension tending to lengthen the working portion and the tension tending to lengthen the standing portion includes a position in which the member is aligned with at least one of the tension tending to lengthen the working portion and the tension tending to lengthen the standing portion.

In yet another embodiment, the member is movable relative to the body and a range of motion of the member relative to the body includes a position in which the member is transverse to the body.

In yet another embodiment, the member is movable relative to the body and a range of motion of the member relative to the body includes at least one position in which the member is aligned with the body.

In yet another embodiment, the member pivots relative to the body.

In yet another aspect of the disclosed technology, yet another system includes a line with a locking portion and a standing portion. The locking portion has a constricted section and a compression section. The system also includes a line lock with a body at least partially bounding a plurality of passageways and a compression limiter. The locking portion of the line is routed through at least some of the passageways so that the constricted section is between the line lock and the compression section. The constricted section is compressed between the compression section and the line lock in response to tension in the line tending to draw the line along the routing along a first direction so that the system resists drawing the line along the first direction except when the compression limiter reduces compression on the constricted section to permit the line to be drawn along the pathway.

In an embodiment, the standing portion couples the system to a structure.

In other embodiments, the standing portion is looped around the structure or encircles the structure.

In yet other embodiments, the standing portion is embedded within the structure, inserted through an anchor embedded in the structure, passed through the structure, or positioned behind the structure.

In yet another embodiment, the length of the standing portion is adjusted to remove slack between the line lock and the structure.

In yet another embodiment, the structure is selected from the group consisting of a soft tissue, a muscle, a cartilage, a cartilage graft, a fascia, a tendon, a ligament, a ligament graft, an anterior cruciate ligament graft, a hard tissue, a bone, an autograft, an allograft, a xenograft, and a synthetic graft.

In yet other embodiments, the compression limiter separates the line lock and the compression section, the line lock and the constricted section, or the compression section and the constricted section.

In yet other embodiments, the compression limiter extends between the line lock and the compression section, the line lock and the constricted section, or the compression section and the constricted section.

In yet another embodiment, the compression limiter has a diameter. The diameter may be between the line lock and the compression section, the line lock and the constricted section, or the compression section and the constricted section in various embodiments. The diameter is larger than a diameter of the constricted section.

In yet another embodiment, the compression limiter is looped around the compression section.

In other embodiments, tension on the compression limiter pulls the compression section away from the line lock or the constricted section.

In yet another embodiment, the compression limiter is looped around the constricted section.

In yet another embodiment, tension on the compression limiter pulls the constricted section away from the line lock.

In yet another embodiment, the compression limiter is coupled to the line lock, the compression section, or the constricted section.

In yet another embodiment, the compression limiter has a filament.

BRIEF DESCRIPTION OF THE DRAWINGS

Various embodiments of the present technology will now be discussed with reference to the appended drawings. It is appreciated that these drawings depict only typical embodiments of the technology and are therefore not to be considered limiting of its scope.

DETAILED DESCRIPTION OF THE PREFERRED EMBODIMENTS

Figure 1:
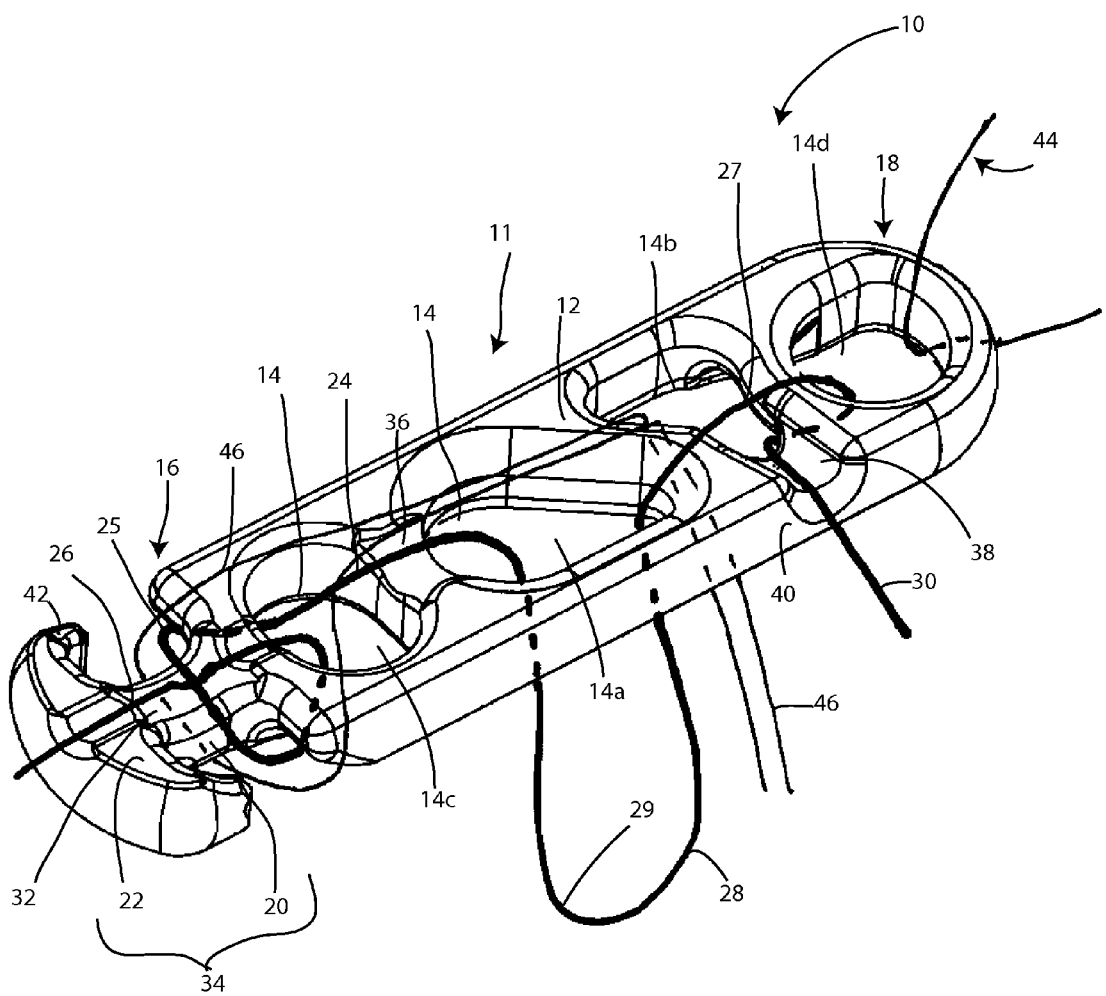
FIG. 1 illustrates a perspective view of a device with a neck and head of the plate, a plurality of passageways through a body of the plate, a line routed through the plurality of passageways, a primary filament and a secondary filament.
Figure 2:
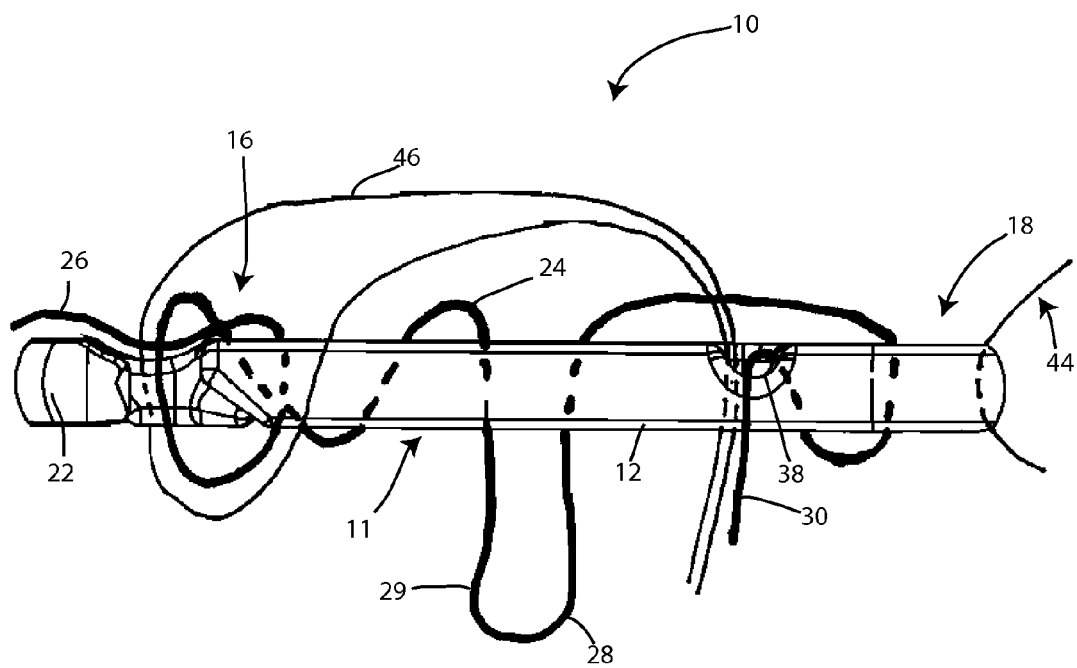
FIG. 2 illustrates a side view of the device, line, and filaments of FIG. 1.

The disclosed systems provide means for "locking" a line or suture at a length without using a knot, such knots being capable of reducing the strength of the line or suture. The systems allow for adjustment of the line/suture/sling length on the back table, reducing the need for multiple sizes or parts. Because of the adjustable nature the tolerance/error band on the line length is lower than competitive devices that use a fixed size and/or length line. Parts of this system may include a zip knot or "wrap" along with plate geometry and hole patterns for routing of a line. The device may also include a loop/cinch with a first loop or lead loop. Other features may include adjustability of a single free end or multiple free ends. Furthermore a first or primary filament and second or secondary filament configurations may be used to flip the plate to secure the device against a bone.

One embodiment is a rectangular piece/plate with rounded ends. One of the ends has a "dogbone" feature for lines and filaments to wrap around. The dogbone feature may comprise two cutouts toward one end of the plate on opposing sides, forming a neck, which give the structure its name as featured in the FIGS. 1-14 and 17-21. FIGS. 15-16 show what may be a dogbone feature, however the dogbone feature may be less pronounced than in the other figures. There may be four holes in the plate; two on each end, and two holes more centrally located in the plate. A line which may be a suture, a cord, or a filament material is passed through the holes to create an adjustable loop/sling to hold an ACL graft or other biological material. The graft line material is fixed to the dogbone end via a looping technique that secures the line to the plate and simultaneously provides a first loop that is configured to be pulled on directly or have a filament passed through this first loop. Such a looping technique may include those as described in U.S. Pat. Nos. 7,594,923, 7,566,339 and 7,150,757 which are herein incorporated by reference. This first loop can be pulled on directly or via secondary filaments to pull or position the plate through a tunnel or hole. A non-looped end, or a free end, of the line material passes around the plate and back under itself to form a self-locking wrap. When the free end of the line is pulled, the adjustable loop, or sling, can be shortened. When the adjustable loop is pulled on, the self-locking wrap cinches itself tighter.

The plate is designed to fit through a bone tunnel and can be inserted via any preferred approach (e.g., medial portal or trans-tibial approaches). A first or primary filament may have a first filament loop created along its length a specified distance from its mid-length, the loop may be stationary but may also move along the length of the first filament. The first filament may have a stationary feature, which may be a knot, at the filament's mid-length. A section of the first filament is looped through the plate body on one side. The secondary filament may pass through the body of the plate or through the first loop of the line. A second filament may be passed through one of the central holes in the body of the plate which may be the same hole that the first loop of the line is passed through. The second or secondary filament may also pass through the first filament loop. The second filament may be fixed to the plate at any specified distance from the central plate hole such as passing the second filament around the dogbone feature of the plate or around the plate in general or through any of the other plate holes. The colors and lengths of the filaments may be configured to ensure the primary filament through the plate hole will be pulled through the bone tunnel to pull up the button past the cortical wall, with the secondary filament parallel with the first loop and graft. Once the plate clears the bone tunnel, the secondary filament is pulled on either trans-tibially or from a medial portal to flip the plate so that the plate is perpendicular to the tunnel and anchors against the bone (plate contact area larger the bone tunnel area). After plate installation one end of the primary filament is pulled through the plate, simultaneously pulling the secondary filament from the bone tunnel and central hole in the body of the plate. The secondary filament is pulled from the plate.

One will appreciate that the secondary filament is not required to pass through a first filament loop and thus the secondary filament may not be removed in conjunction with removal of the primary filament. The secondary filament may pass through the bone tunnel and after installation of the plate the secondary filament may be removed through the plate similar to the primary filament.

This device may be used to hold an ACL graft and the graft may be soft or hard tissue. In addition this device is not limited to the ACL or knee and may have other applications in other parts of the body, such as the shoulder, elbow and ankle.

Referring to FIGS. 1-5, a fixation device 10 is portrayed with a plate 11, a line 24 and filaments 44, 46. The plate 11 may be substantially rectangular and may comprise a body 12 which may have rounded first end 16 and a rounded second end 18. The body may include a plurality of passageways 14 configured to receive the line 24 and first and second filaments 44, 46. The plurality of passageways 14 may be partially or entirely bounded by the plate 11. The plate may also comprise a neck 20 extending longitudinally from the first end 16 of the body 12; however, the neck 20 may extend from either the first end 16 or the second end 18, or both. The neck 20 may be thinner than the body 12 of the plate 11 in at least one plane or the neck 20 may have a smaller circumference than the body 12 of the plate 11. Extending longitudinally from the neck is a head 22 which may be thicker than the neck 20 in at least one plane or may have a greater cross-sectional diameter in at least one plane than the neck 20. The head 22 may also extend from the neck in at least one plane substantially perpendicular to the neck 20. The head 22 may have a substantially similar thickness as the body 12 of the plate or may have a substantially similar cross-sectional diameter in at least one plane as the body 12 of the plate 11. The neck 20 and head 22 of the plate 11 create a dogbone feature 34 on one end of the plate 11. The head 22 may be rounded on the end opposite the neck 20.

The plate 11 may also comprise grooves 36 throughout the plate. The grooves 36 may extend between passageways 14 or between a passageway 14 and a periphery 40 of the plate 11 or even grooves 36 from between the head 22 and neck 20 and the neck 20 and the body 12. The grooves 36 may also reside on the top, sides or bottom of the plate 11. The plate 11 is designed to fit through a bone tunnel and can be inserted via any preferred approach (e.g., medial portal or trans-tibial approaches). The plate may be comprised of biocompatible materials including but not limited to titanium, stainless steel, cobalt chrome, PEEK, PLLA, polymer/ceramic composites, polymers, co-polymers, or alloys or a combination of those mentions herein. In addition any material used for the plate may also be coated with bioactive or supportive materials.

The plurality of passageways 14 may be generally rounded and are capable of receiving at least one line. The plurality of passageways 14 may comprise four passageways that are configured to receive the line 24 and are shaped and patterned for the routing of the line through the passageways 14. The passageways 14 may be substantially on the body 12 of the plate 11; however in an alternate embodiment the neck 20 may also comprise a passageway 14. Of the four passageways, those disposed more laterally may comprise a more ovoid shape and those passageways disposed more medially may comprise a more triangular or tear-drop shape. The shapes of the plurality of passageways 14 are selected to enhance the routing and self-locking of the line 24 to the plate 11. The tear-drop shape of at least one of the plurality of passageways 14 may further enhance the locking of the line 24 for the adjustable loop 29. The ovoid shape of at least one of the plurality of passageways 14 may allow for multiple passes of the line 24 through the same passageway while minimizing total passageway area. The plurality of passageways 14 may also taper or enlarge from the top to the bottom of the plate 11 or the plurality of passageways 14 may taper or enlarge from the bottom to the top of the plate 11.

The neck 20 is a smaller circumference than the body 12, or is thinner than the body in at least one plane, to maintain the line 24. The smaller circumference may also provide protection of the lines as they pass through the cutouts that create the neck to prevent the lines from rubbing against the walls of a bone tunnel when passing the plate 11 through the bone tunnel.

The head 22 of the plate 11 may comprise flanges or fins 42 which extend back toward the body 12 of the plate 11. These flanges 42 may add greater security of the line 24 and the second filament 46 preventing withdrawal of the second filament 46 or the line 24 over the head 22. The flanges 42 may also provide added protection of the line 24 and second filament 46 during passage of the plate through the bone tunnel.

The line 24 of the device 10 is routed through the passageways 14 to create a self-locking slide. The line 24 may be comprised of metal, polymer, composite or suture and may be woven or braided. The line may comprise a first portion, which may be a first working portion 26, and a second portion, which may be a second working portion 30. Both of the first and second working portions 26, 30 may have free ends. Between the first working portion 26 and the second working portion 30 is an intermediate portion 28 which may comprise an adjustable loop 29. The first working portion 26 is routed along a first pathway. The first pathway may comprise routing the first working portion up through a first medially located passageway 14a, through at least one of the grooves 36, down through a first laterally located passageway 14c, around the neck 20, up through the first laterally located passageway 14c and passed underneath the portion of the line around the neck 20. The neck 20 may comprise a neck groove 32 that the line passes through underneath the portion of the line 24 that is wrapped around the neck 20. A first compression section 25 is formed with the line passing underneath the portion of the line that passes around the neck 20 wherein when the first working portion 26 is pulled tight the compression section 25 pushes a portion of the line against the neck groove 32 of the neck 20 self-locking the line 24 against the plate 11. This compression section 25 of the line creates a one-way slide allowing for the first working portion 26 to be advanced only along one direction, the one direction defined by the routing of the first working portion 26.

The second working portion 30 is routed along a second pathway. The second pathway may comprise routing the second working portion up through the first medially located passageway 14a, passed over the top of a periphery groove 38, the periphery groove 38 extending from a second medially located passageway 14b to the periphery 40 of the plate. The second working portion 30 is then passed down through the second laterally located passageway 14d, up through the second medially located passageway 14b and underneath the portion of the line 24 that passed over the periphery groove 38. A second compression section 27 is formed with the line passing underneath the portion of the line that passes over the top of the periphery groove 38 wherein when the second working portion 28 is pulled tight the compression section 27 pushes a portion of the line against the periphery groove 38 of the plate 11 self locking the line against the plate 11. This compression section 27 of the line creates a one-way slide allowing for the second working portion 30 to be advanced only along one direction, the one direction defined by the routing of the second working portion 30.

The adjustable loop 29 of the intermediate portion 28 of the line 24 is configured to hold a graft (not shown). The graft may be an ACL graft and may be a soft or hard tissue. The graft is looped around the adjustable loop 29 to retain the graft. By pulling on either the first working portion 26 or the second working portion 30, or both, the adjustable loop 29 reduces in size pulling the graft closer to the plate 11. The adjustable loop 29 is unable to increase in size after the graft is captured by the adjustable loop 29 and the line 24 is routed through the plate 11 because the routing of the line 24 forms a one-way slide so only reduction of the adjustable loop 29 occurs.

The first filament 44 passes through the second laterally positioned passageway 14d and is used to pull the plate 11 through the bone tunnel along a longitudinal axis of the plate 11. The second filament 46 may be routed around the neck 20, creating a loop around the neck 20, of the plate 11 and then passed through the second medially positioned passageway 14b. The second filament 46 is used to toggle the plate 11 after the plate 11 passes through the bone tunnel. After passing through the bone tunnel the second filament 46 may remain in the bone tunnel. The second filament 46 is pulled and the plate 11 toggles so that the longitudinal axis of the plate 11 is perpendicular to the bone tunnel. After the plate 11 is positioned on a cortical side of a bone the first and second filaments 44, 46 may be removed by pulling on one end of each filament. After positioning of the plate 11 the first working portion 26 or the second working portion 30, or both, are pulled to reduce the size of the adjustable loop 29 thereby creating greater tension in the graft and further cinching the plate 11 against the cortical side of the bone.

Figure 3:
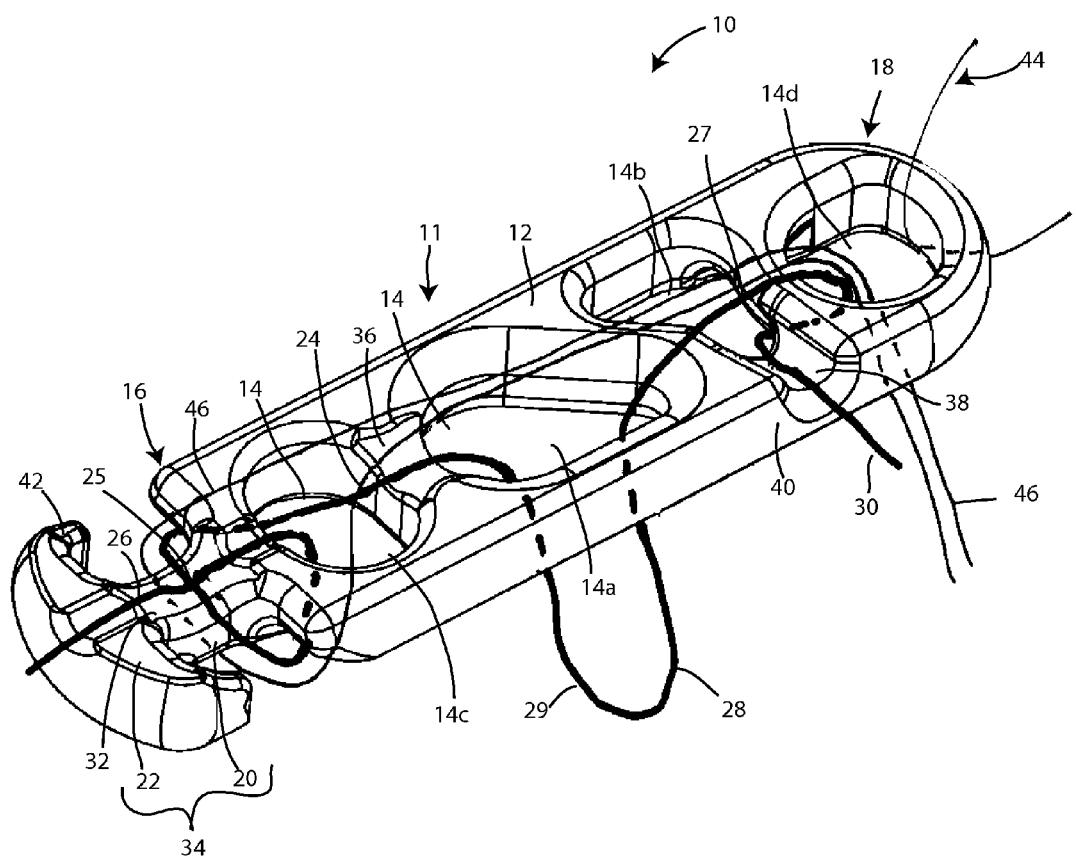
FIG. 3 illustrates a perspective view of the device of FIG. 1 with a plate, the plate with a head, neck, body and a plurality of passageways and the line routed through the plurality of passageways with a primary and secondary filament, the secondary filament routed differently than in FIGS. 1 and 2.

The routing of the second filament 46 may be done in a plurality of ways. Referring to FIG. 3, the second filament 46 may be routed around the neck 20, creating a loop around the neck 20, similar to the embodiment in FIG. 1. The second filament 46 then passes through the second laterally positioned passageway 14d. The same effect is achieved with this routing as that previously described in that the second filament 46 is used to toggle the plate 11 after passing through the bone tunnel. Similar to the previous routing, after passing through the bone tunnel the second filament 46 may remain in the bone tunnel. After the plate 11 is positioned on the cortical side of the bone the second filament 46 is removed.

Figure 4:
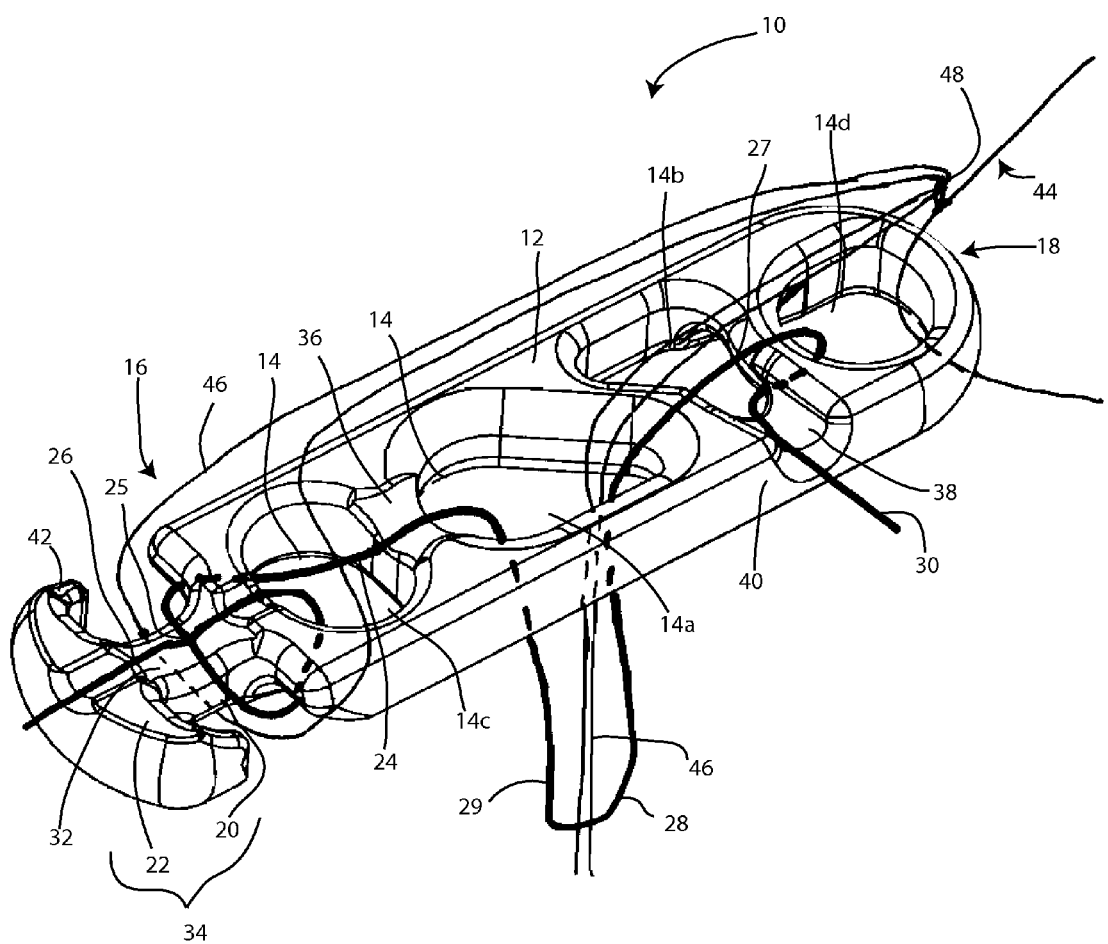
FIG. 4 illustrates a perspective view of the device of FIG. 1 with a plate, the plate with a head, neck, body and a plurality of passageways and the line routed through the plurality of passageways with a primary and secondary filament, the secondary filament routed differently than in FIGS. 1 and 3.

Referring to FIG. 4, the second filament 46 may be routed around the neck 20, creating a loop around the neck 20, and then the second filament passed slidably through a first filament loop 48 of the first filament 44. The first filament loop 48 may be static. The second filament 46 may then be routed through any of the plurality of passageways 14. After passage of the plate 11 through the tunnel the second filament 46 is again used to toggle the plate 11 so that the longitudinal axis of the plate is perpendicular to the bone tunnel. Similar to the previously described routing, after passing through the bone tunnel the second filament 46 may remain in the bone tunnel. After positioning of the plate 11, the first filament 44 may be removed thereby removing the second filament 46 as well because the second loop is still within the first filament loop 48.

Figure 5:
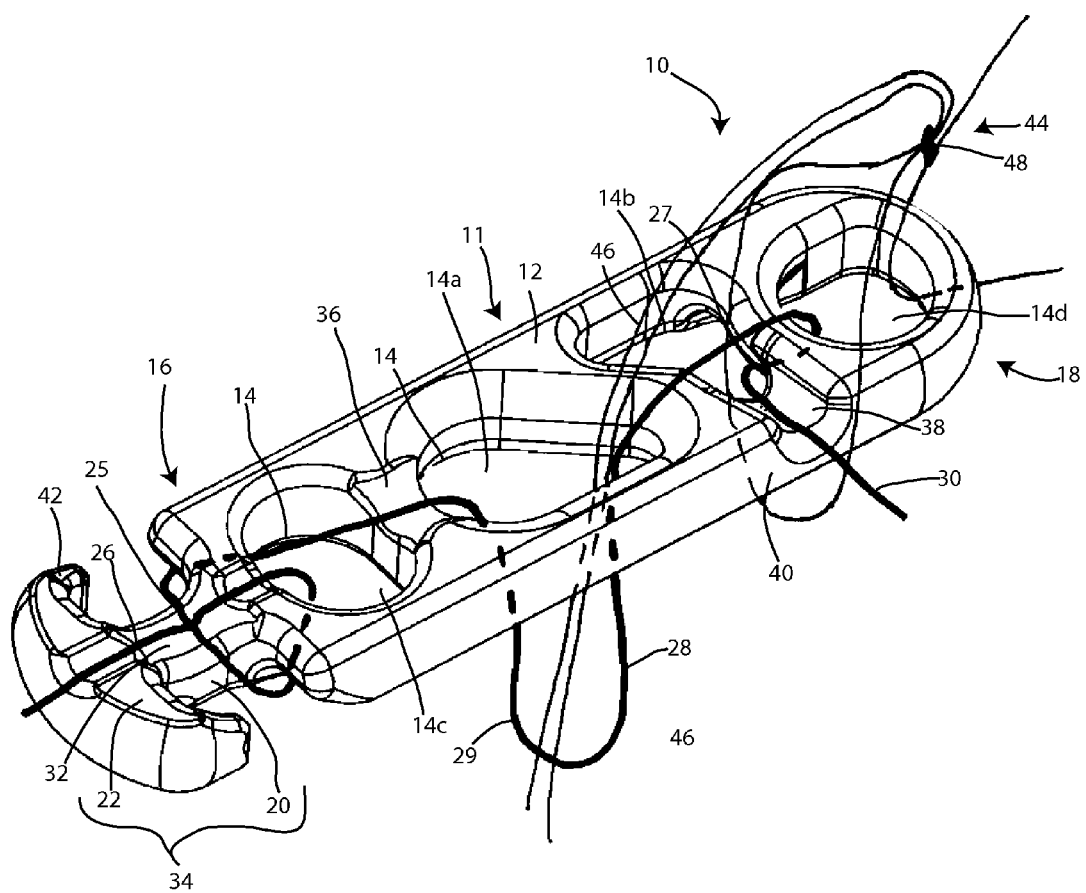
FIG. 5 illustrates a perspective view of the device of FIG. 1 with a plate, the plate with a head, neck, body and a plurality of passageways and the line routed through the plurality of passageways with a primary and secondary filament, the secondary filament routed differently than in FIGS. 1, 3 and 4.

Referring to FIG. 5, the second filament 46 may be routed through any of the plurality of passageways 14 creating a loop around the intended passageway. The filament is then routed through the first filament loop 48 of the first filament 44. The second filament 46 may then be routed through any of the plurality of passageways 14. Once the plate 11 clears the bone tunnel, the second filament 46 is pulled on (trans-tibially or from the medial portal) to flip the plate so that the plate 11 is perpendicular to the bone tunnel and anchors against the bone with the plate contact area being larger than the bone tunnel. Similar to the previously described routing, after passing through the bone tunnel the second filament 46 may remain in the bone tunnel. Similar to the removal of the first filament 44 in the preceding paragraph, after positioning of the plate 11, the first filament 44 may be removed thereby removing the second filament 46 as well because the second loop is still within the first filament loop 48.

After the plate 11 is secured against the cortical bone, the filaments 44, 46 are removed and the plate 11 is cinched and the adjustable loop 29 adjusted to the appropriate length and tension the free ends of the first and second working portions 26, 30 may be cut to shorter lengths.

Figure 6:
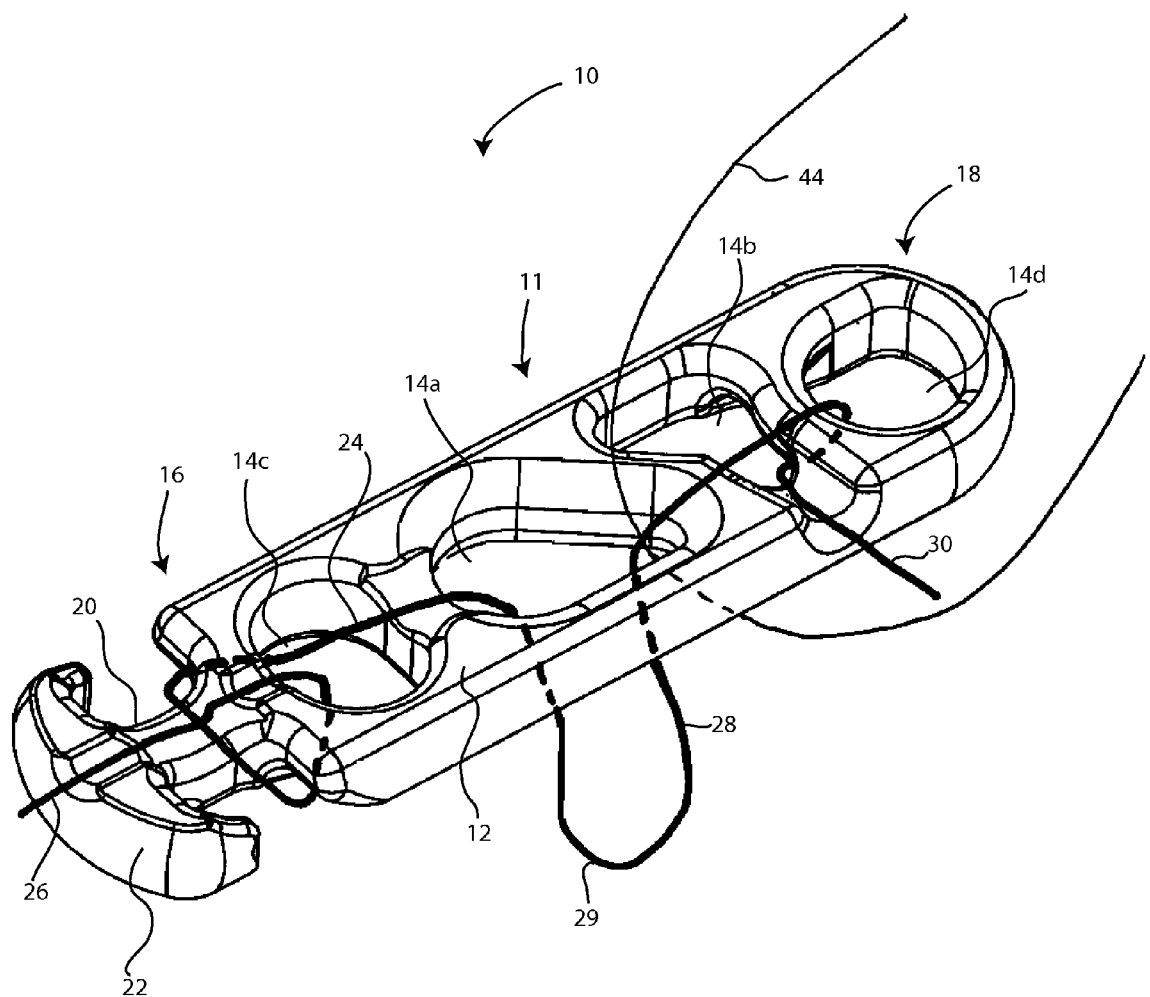
FIG. 6 illustrates a perspective view of the device of FIG. 1 with a plate, the plate with a head, neck, body and a plurality of passageways and the line routed through the plurality of passageways with only a primary filament, the primary filament routed differently than in FIGS. 1, 3, 4 and 5.

Referring to FIG. 6, all of the features previously disclosed are substantially the same; however only a one filament, the first filament 44, is used and passed through the more centrally located first medial passageway 14a. The first filament 44 passes through the first medial passageway 14a. The plate 11 is inserted in a longitudinal direction, substantially parallel to the axis of the bone tunnel, into the bone tunnel. Pulling on the first filament through the bone tunnel the plate 11 passes through the bone tunnel and after clearing the cortical side of the bone the plate 11 toggles automatically, wherein the longitudinal direction of the plate is substantially perpendicular to the axis of the bone tunnel. Because of the placement of the first filament 44 through the first medial passageway 14a, the plate 11 naturally tends to return to a non-parallel state between the plate 11 and the bone tunnel. In this embodiment a second filament is not needed to toggle the plate 11.

Figure 7:
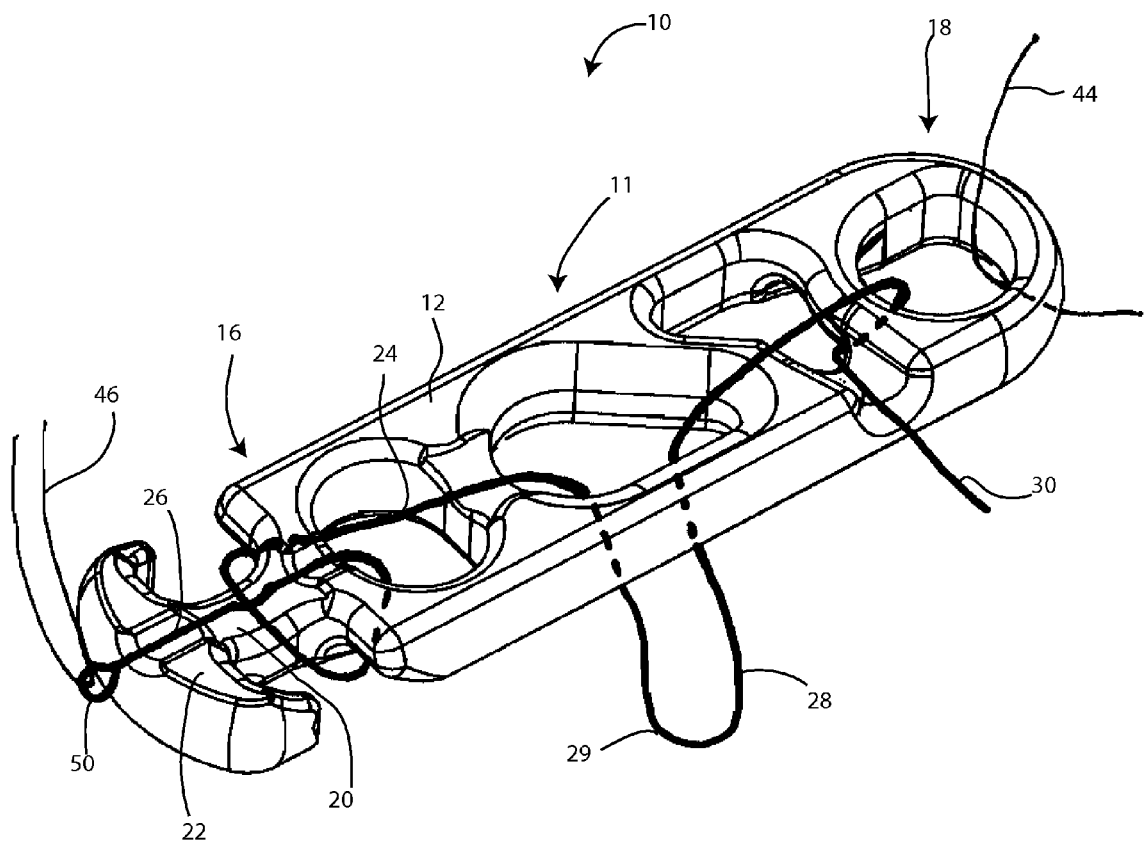
FIG. 7 illustrates a perspective view of an alternate embodiment of FIG. 1 with a neck, a head and a body of the plate, the body with a plurality of passageways and a line routed through the plurality of passageways, and a plurality of grooves, the line comprising a first loop or eyelet at one end.

Referring to FIG. 7, all of the features previously disclosed are substantially the same to this embodiment with the exception of the first working portion 26 may comprise a first loop 50 instead of a free end. The first loop 50 may be an eyelet. The first loop 50 may be woven or braided into the cord or the first loop 50 may be a thicker cord with separate fibers of the cord. The first loop 50 may also use an adhesive in the fibers to help maintain the structure of the loop. The first loop 50 may also be created by using the free end of the first working portion 26 and crimping the free end with a crimp (not shown) to another portion of the first working portion 26 to create a loop. The crimp could be metal, polymer or any other biocompatible materials strong enough to hold the line 24 to form the first loop 50. The first loop 50 may be held tightly against the plate 11 or may be kept at a distance from the plate 11.

The first loop 50 may be configured to receive the second filament 46. The second filament 46 is looped through the first loop 50 and is used to toggle the plate 11 after passage through the bone tunnel. The second filament 46 through the first loop 50 provides certain advantages when pulling the plate 11 through the bone tunnel including increased slidability of the second filament 46 and may provide an offset distance from the plate 11 to improve flipping of the plate 11. Furthermore the first loop 50 may allow for slidability of the second filament 46 preventing the second filament 46 from getting stuck or damaged between the plate 11 and the bone.

Figure 8:
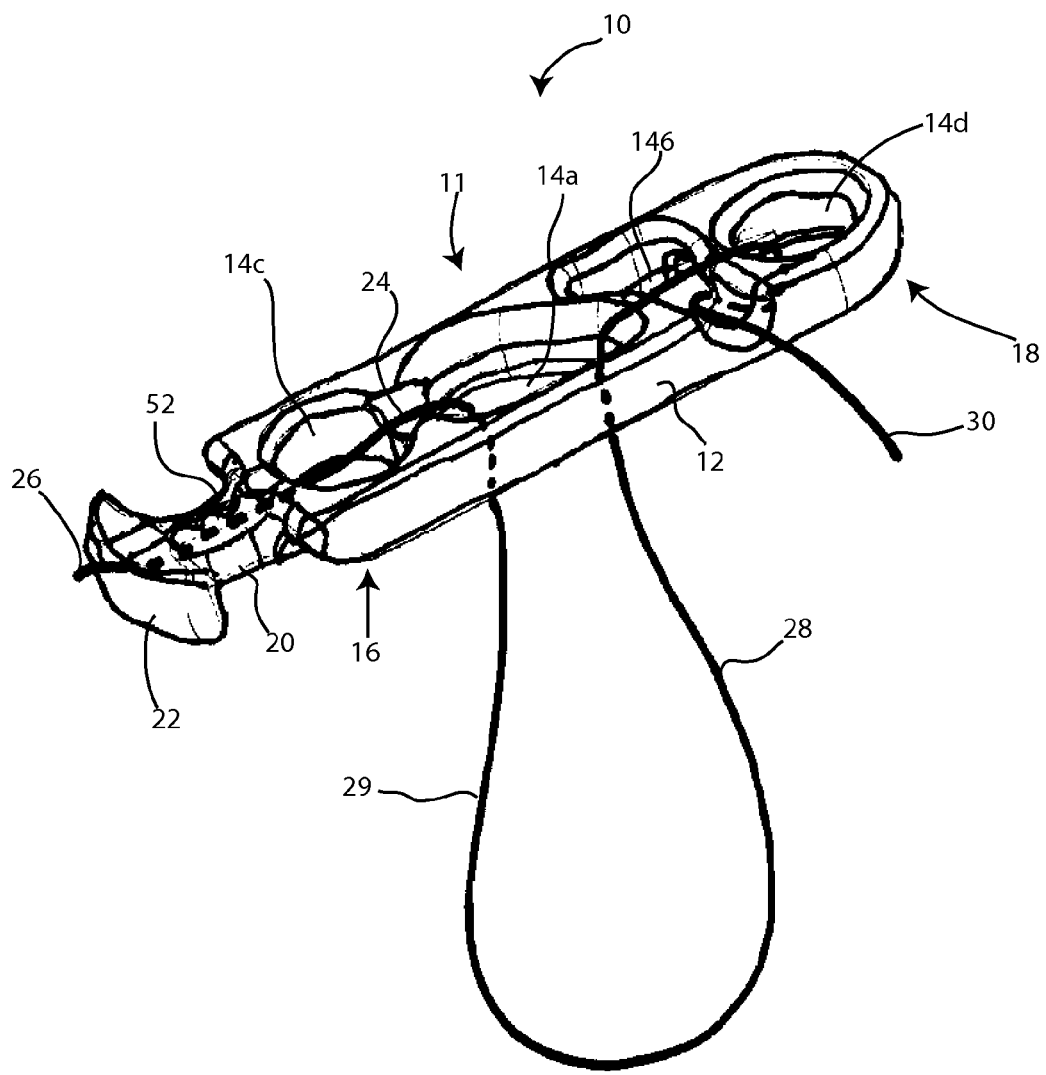
FIG. 8 illustrates a perspective view of an alternate embodiment of the device of FIG. 1, with a plate having a head, a neck and a body, the body with a plurality of passageways and a line routed through the plurality of passageways, and a crimp on the neck of the plate.

Referring to FIG. 8, a device 10 is depicted with a slight different head 22 extending from the neck 20. In this embodiment the head 22 may not include the flanges or fins 42 as depicted in the previous embodiments (FIGS. 1-7). Furthermore, this embodiment may include a crimp 52 on the dogbone end 34, wherein the first working portion 26 of the line 24 passes through the neck groove 32 and is secured to the plate 11 on the neck 22 or the dogbone end 34 through the use of the crimp 52. The crimp 52 would substantially encircle the neck 20 and the first working portion 26 of the line 24 to the plate 11. The crimp 52 may be comprised of any biocompatible material including polymer, composite or metal. A further distinguishing feature of this embodiment is that the first working portion 26 may or may not be routed in the same or similar manner as the routing in the previous embodiment (FIGS. 1-7). With the FIG. 8 embodiment the first working portion 26 may simply pass up through the first medial passageway 14a but may not pass completely back down and through the first lateral passageway 14c, but rather simply pass through the neck groove 32 and then be secured to the plate 11 with the crimp 52. The second working portion 30 of the line 24 is routed in substantially the same manner as described in the previous embodiments described in FIGS. 1-7 with the same routing of the line 24, the same adjustable loop 29 of the intermediate portion 28 and the second compression section 27 which holds a portion of the line 24 to create a one-way slide.

First and second filaments 44, 46 (not shown in FIG. 8) may be routed around and through the plate 11 in any manner as previously described herein. Likewise inserting the plate 11 into the bone tunnel, passing the plate 11 through the bone tunnel, toggling the plate 11 after passage through the bone tunnel, cinching the plate to the cortical side of the bone and removing the filaments 44, 46 from the plate may all be accomplished in any of the ways as previously described herein.

Figure 9:
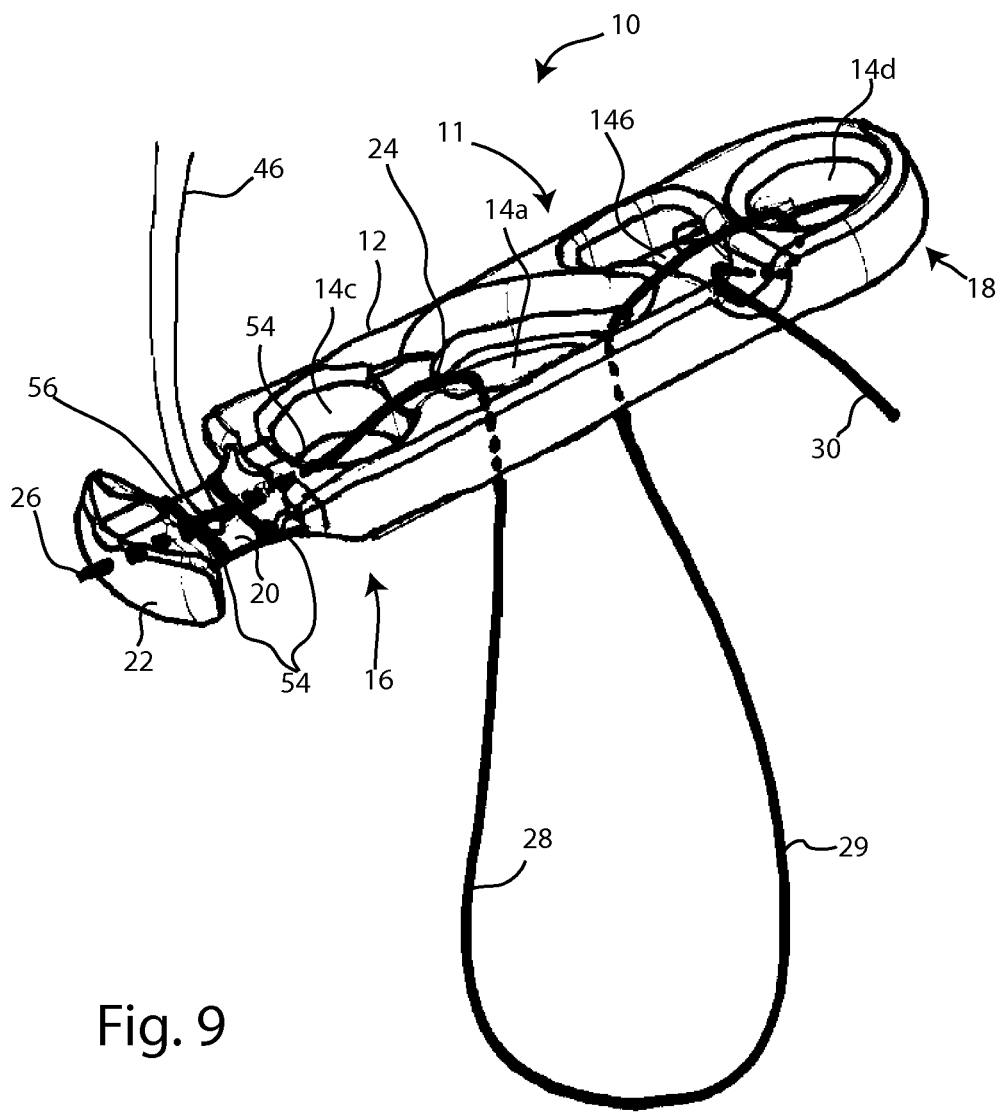
FIG. 9 illustrates a perspective view of an alternate embodiment of the device of FIG. 1, with a plate having a head, a neck and a body, the body with a plurality of passageways and a line routed through the plurality of passageways, and a hole passing longitudinally through the neck from a lateral passageway with an opening allowing a filament to be looped around the line and two pins holding the line in place across the opening.

Referring to FIG. 9, a device 10 is depicted with the nearly the same plate 11 configuration as that of FIG. 8; however, in this embodiment there is a neck hole 54 that passes from the first lateral passageway 14c through the neck 20 and out of the head 22. The neck 20 may include an opening with two transverse pins 55. The first working portion 26 of the line 24 may pass through the neck hole 54 wherein a portion of the first working portion 26 is exposed in a neck opening 56. The neck opening 56 may be defined by two transverse pins 55 that are substantially perpendicular to the longitudinal axis of the plate 11. The transverse pins 55 may retain the line 24 and prevent it from withdrawal from the plate 11. The first filament 44 (not shown in FIG. 9) may be passed through at least one of the plurality of passageways 14. The second filament 46 may pass around the exposed portion of the first working portion 26 in the neck opening 56 and is retained by the exposed portion of the first working portion 26. The first filament 44 (not shown in FIG. 9) may be passed through at least one of the plurality of passageways 14. The second working portion 30 of the line 24 is routed in substantially the same manner as described in the previous embodiments described in FIGS. 1-7 with the same routing of the line 24, the same adjustable loop 29 of the intermediate portion 28 and the second compression section 27 which holds a portion of the line 24 to create a one-way slide.

A method of inserting the plate 11 into the bone tunnel, passing the plate 11 through the bone tunnel, toggling the plate 11 after passage through the bone tunnel, cinching the plate 11 to the cortical side of the bone and removing the filaments 44, 46 from the plate may be accomplished in any of the ways as previously described herein.

Figure 10:
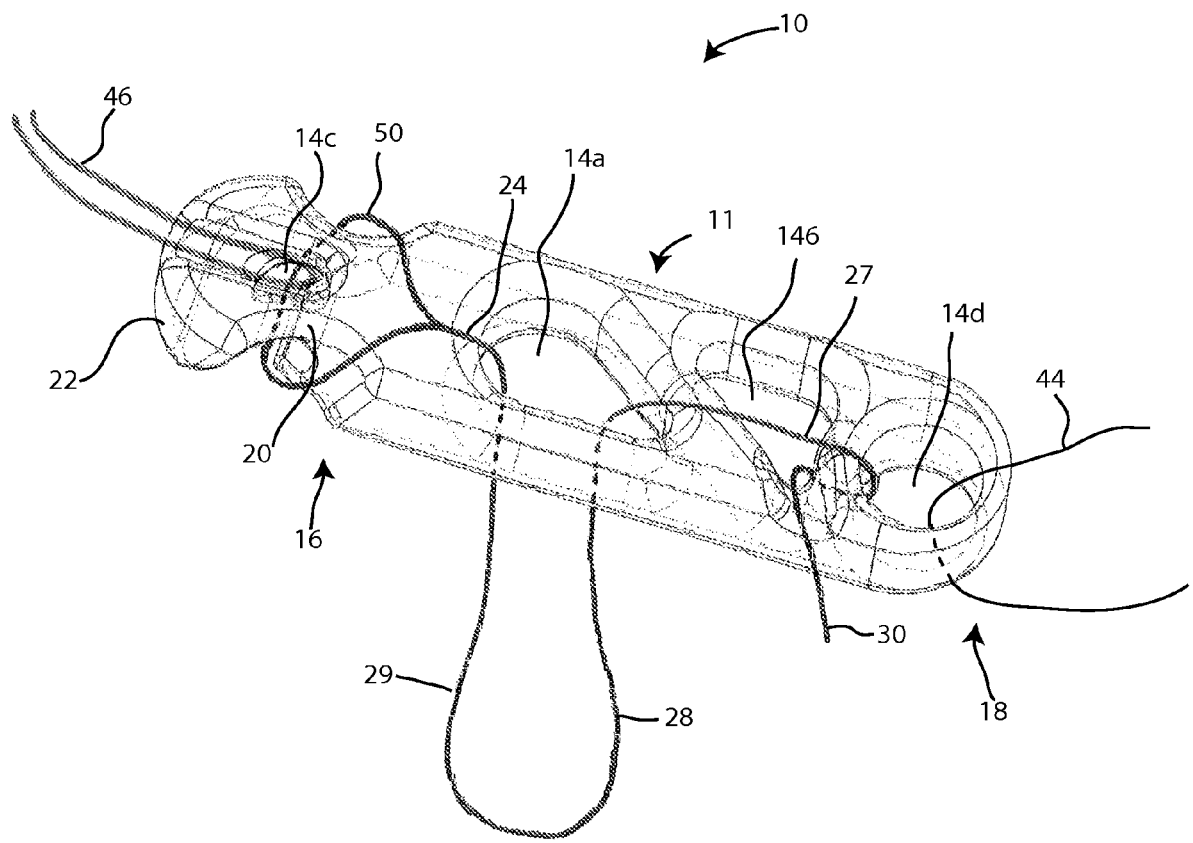
FIG. 10 illustrates a perspective view of an alternate embodiment of the device of FIG. 1, with a plate having a head, a neck and a body, the body with a plurality of passageways and a line routed through the plurality of passageways, one of the passageways on the neck of the plate and a loop of the line wrapped around the neck and a filament passing through the neck passageway and looped around the line so the filament is retained by the line.

Referring to FIG. 10, a device 10 is depicted with the plurality of passageways 14 as previously described; however, in this embodiment one of the plurality of passageways is positioned in the neck 20 of the plate 11. The second working portion 30 of the line 24 is routed in substantially the same manner as described in the previous embodiments described in FIGS. 1-7 with the same routing of the line 24, the same adjustable loop 29 of the intermediate portion 28 and the second compression section 27 which holds a portion of the line 24 to create a one-way slide. The first working portion 26 of the line 24 includes the first loop 50 as described in FIG. 7. In this embodiment the first loop 50 is not secured to the plate through a first compression section 25 as previously described; rather, the first loop 50 is lassoed around the neck 20. The second filament 46 is then able to pass through the passageway in the neck, the first lateral passageway 14c, and loop around the first loop 50, the first loop 50 retaining the second filament. The first filament 44 is passed through the second lateral passageway 14d and the filaments 44, 46 are used to pass the plate 11 and toggle the plate 11 in any manner as previously described herein. It will be appreciated that the first filament 44 may pass through any of the remaining plurality of passageways 14 of the plate 11 except for the first lateral passageway 14c.

Alternate embodiments of the plate are depicted in FIGS. 11-21. In each of the FIGS. 11-21 the line 24 has not been shown neither do the figures show the first and second filaments 44, 46. It should be understood that the line 24 and filaments 44, 46 may be used for those embodiment described and illustrated for FIGS. 11-21 in the same manner as any previously disclosed embodiment in the paragraphs and illustrations above. For the avoidance of doubt, the line may comprise two free ends or one free end and a loop or further still one free end and another securing means as described above such as crimps, pins, loops or clamps. In addition each of these embodiments may comprise a looped end on the first working portion 26 and a free end on the second working portion 30 as set forth above.

Figure 11:
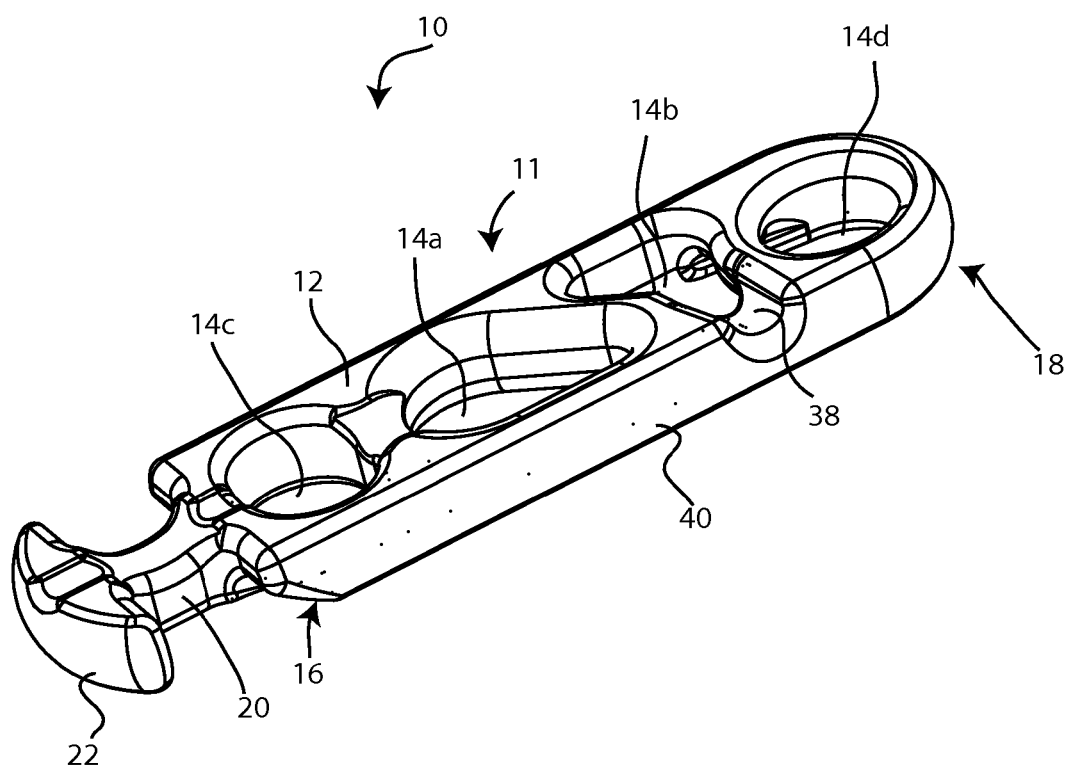
FIG. 11 illustrates a perspective view of an alternate embodiment of the plate of FIGS. 1-7, with the plate having a head, a neck and a body, the body with a plurality of passageways for receiving at least one line, without the line depicted.
Figure 12:
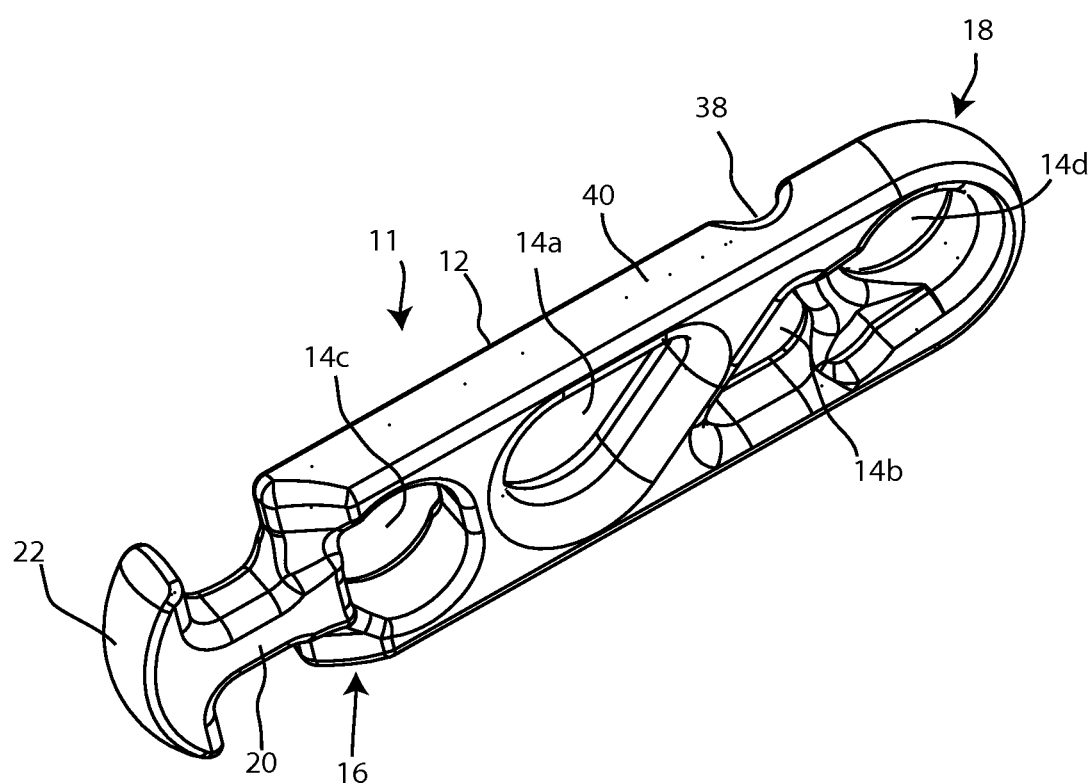
FIG. 12 illustrates a bottom perspective view of the plate of FIG. 11, with the plate having a head, a neck and a body, the body with a plurality of passageways for receiving at least one line.

Referring to FIGS. 11-12, the plate 11 is the same as shown in FIGS. 8 and 9 without the line 24 and the first and second filaments 44, 46 depicted. The line 24 and filaments 44, 46 may be used in this embodiment in any of the previously described methods found herein.

The features in this embodiment are very similar to the previous embodiment of the plate in FIGS. 1-7 with the exception that the plurality of passageways 14 may have slightly different shapes where the substantially triangular or tear-drop shaped passageways may have other bends and the ovoid passageways may be more circular. Other distinguishing features of this embodiment of the plate 11 are the shape and features of the head 22 of the dogbone feature 34. Like the previous embodiment the head 22 has a greater cross-sectional diameter than the neck 20 in at least one plane. Whereas the previous embodiment may have comprised flanges or fins 42 extending back toward the body 12 of the plate 11 giving the dogbone feature 34 an almost anchor like look, this embodiment does not require the fins 42 but rather the head 22 may only extend outward from the neck 20 in at least one plane perpendicular to the longitudinal axis of the plate 11. The head 22 may also be rounded on one end opposite from the neck 20. The same features found in the previous embodiment hold true for this embodiment in that there are grooves 36 which may pass between the plurality of passageways and this embodiment may also include a periphery groove 38 extending from one of the second medially passageway 14b to the periphery 40 to receive the second working portion 30 of the line 24.

Figure 13:
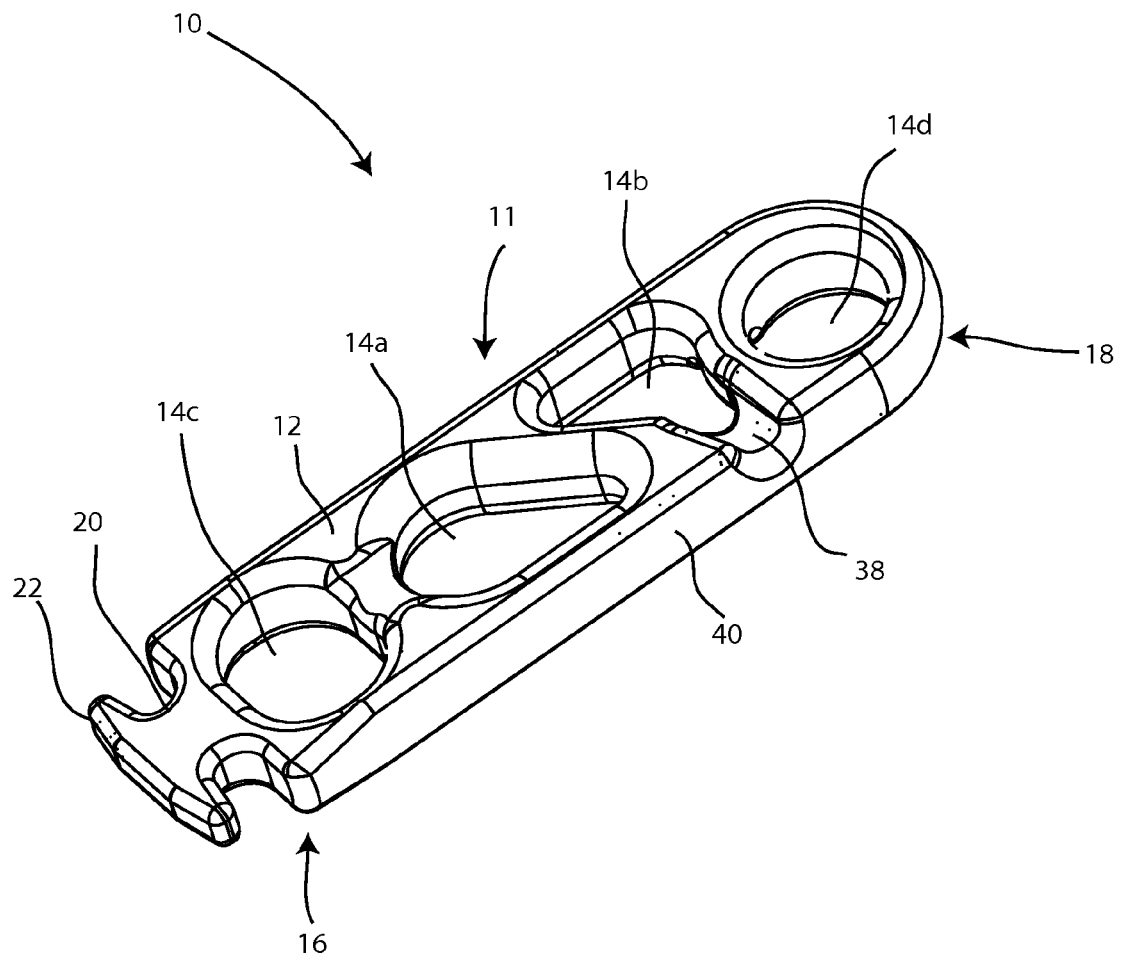
FIG. 13 illustrates a perspective view of an alternate embodiment of the plate of FIGS. 1-7, with the plate having a head, a neck and a body, the body with a plurality of passageways for receiving at least one line, without the line depicted.
Figure 14:
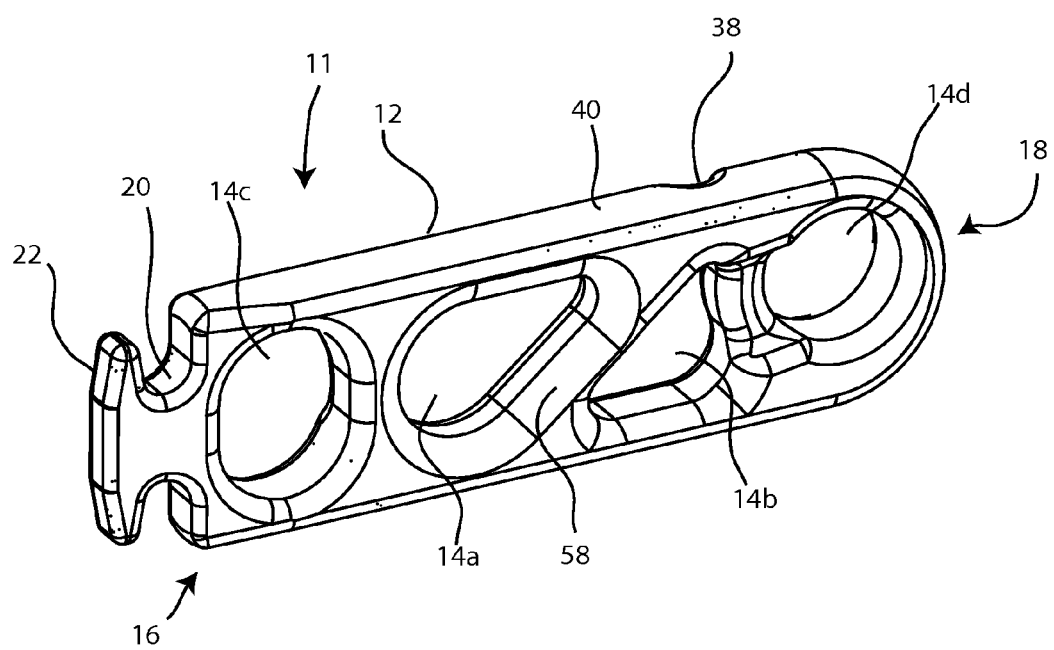
FIG. 14 illustrates a bottom perspective view of the plate of FIG. 13, with the plate having a head, a neck and a body, the body with a plurality of passageways for receiving at least one line and curved ends of the passageways adjacent to one another.
Figure 15:
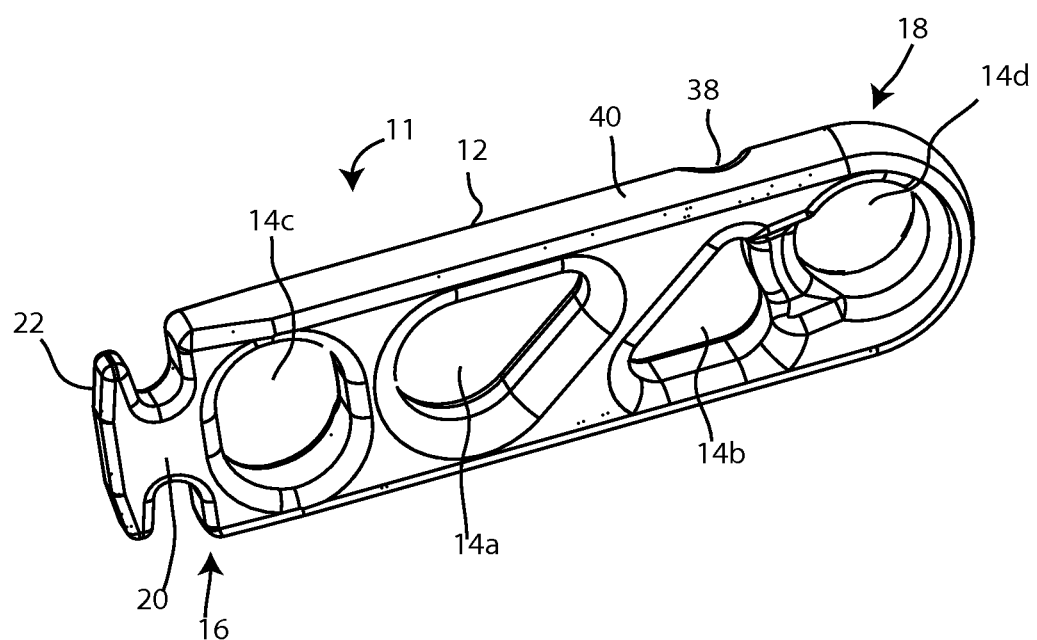
FIG. 15 illustrates a bottom perspective view of the plate of FIG. 13, with the plate having a head, a neck and a body, the body with a plurality of passageways for receiving at least one line and curved ends of the passageways separated by a portion of the body of the plate.
Figure 16:
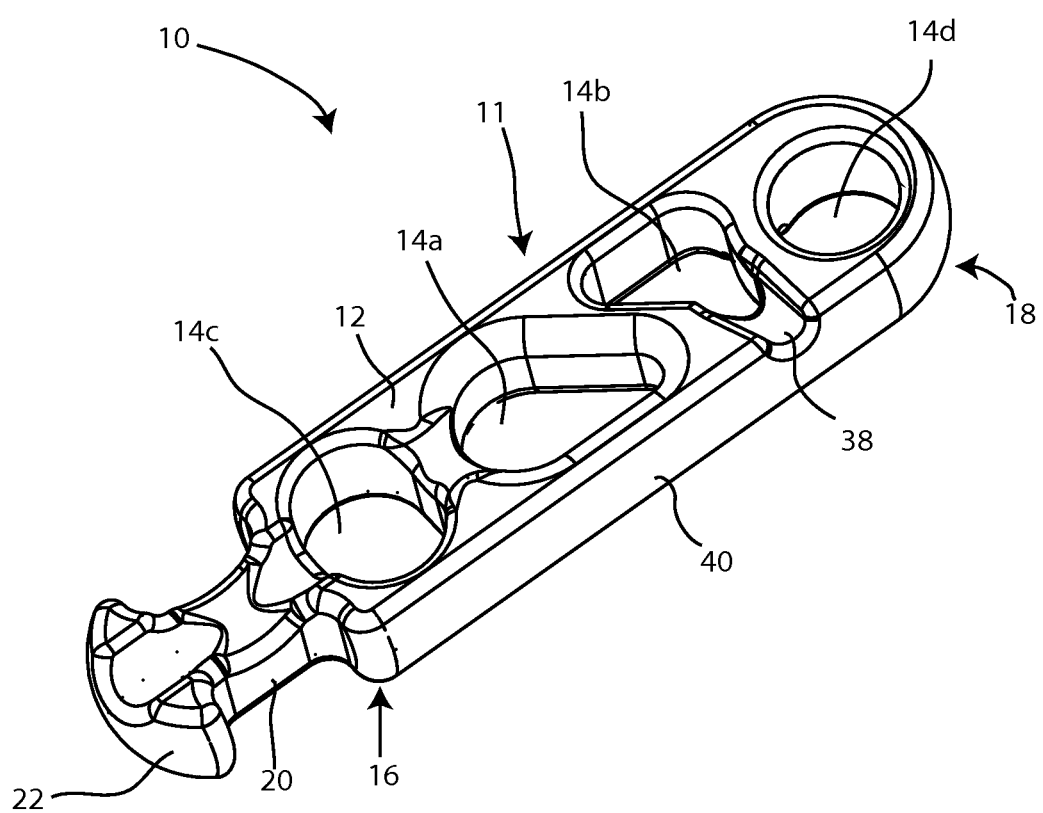
FIG. 16 illustrates a perspective view of an alternate embodiment of the plate of FIGS. 1-7, with the plate having a head, a neck and a body, the body with a plurality of passageways for receiving at least one line, without the line depicted.

Referring to FIGS. 13-15, the plate 11 may include similar features as the previously described plates with passageways and grooves; however, in this embodiment the neck 20 may be shorter than in the previous embodiments and the head 22 extending from the neck 20 creating the dogbone feature 34 has previously set forth. The head 22 may have a larger circumference than the neck 20 but smaller than the body 12 of the plate 11.

Referring to FIG. 14, the plurality of passageways 14 may comprise curved ends 58 that allow for easy passage of the line 24 through the plurality of passageways 14. The curved ends 58 of the plurality of passageways 14 may extend into each other as depicted between the first medial passageways 14a and second medial passageway 14b. Alternately, as depicted in FIG. 15 between the first medial passageways 14a and second medial passageway 14b, the curved ends 58 may be separated by part of the body 12 of the plate 11.

Figure 17:
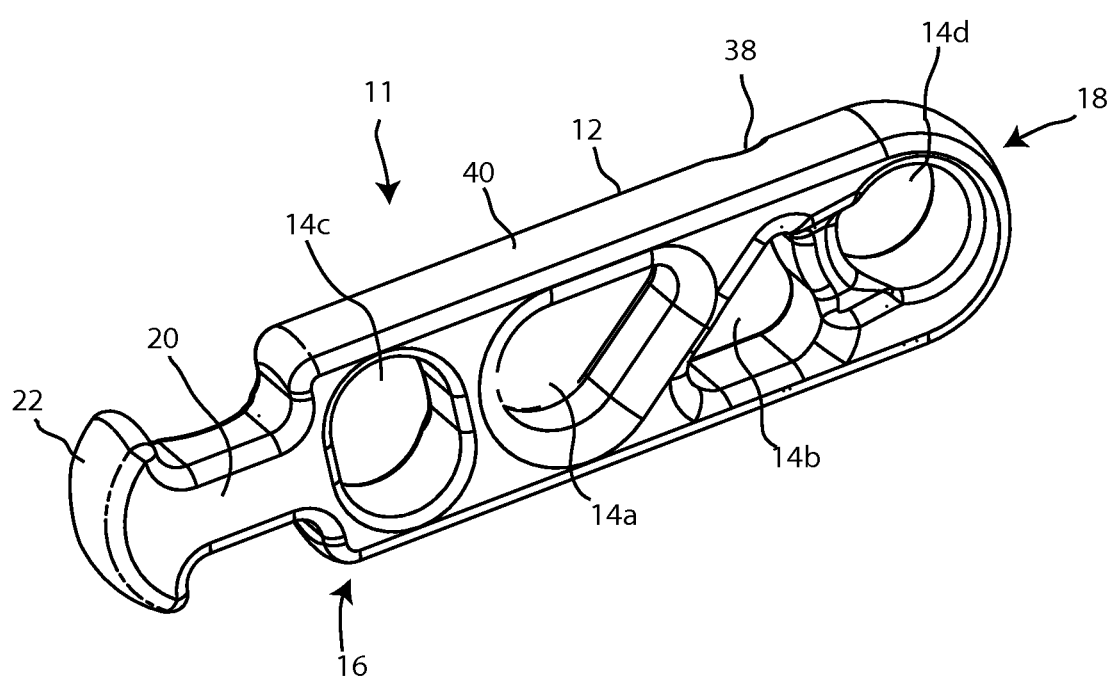
FIG. 17 illustrates a bottom perspective view of the plate of FIG. 16, with the plate having a head, a neck and a body, the body with a plurality of passageways for receiving at least one line.

Referring to FIGS. 16-17, this alternate plate 11 embodiment comprises substantially all of the features as previously described herein with a neck 20 and head 22 creating a dogbone feature 34. The neck may have a substantially smaller cross-sectional diameter than the body 12 of the plate 11 and the head 22 may have a larger circumference than the neck 11; however the head 22 may have a smaller cross sectional diameter in at least one plane than the body 12 of the plate 11. The shapes of the plurality of passageways 14 may be substantially the same as the previous embodiments with the lateral passageways 14c, 14d maintaining a substantially ovoid or circular shape and the medial passageways 14a, 14b maintaining a substantially triangular or tear-drop shape.

Figure 18:
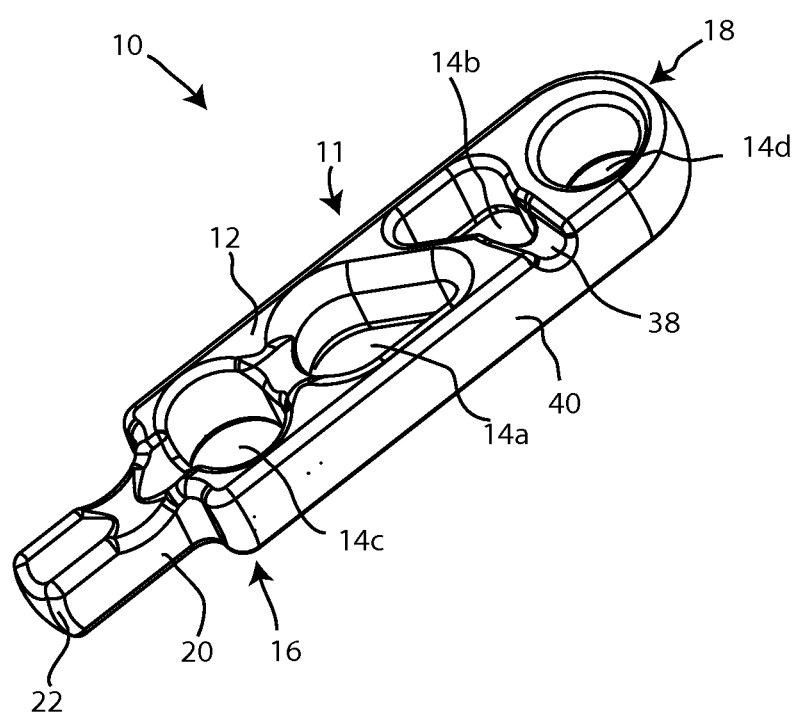
FIG. 18 illustrates a perspective view of an alternate embodiment of the plate of FIGS. 1-7, with the plate having a head, a neck, resembling a single post, and a body, the body with a plurality of passageways for receiving at least one line, without the line depicted.

Referring to FIG. 18, this alternate embodiment of the plate 11 may comprise features substantially similar to those already described herein. However, the neck 20 and head 22 may of the dogbone feature 34 may have substantially the same cross-sectional diameter in at least one plane. The neck 20 extends from at least one end of the body 12 of the plate 11 and the head 22 extends from the neck 20 but the extension may look like a singular post extending from the body 12 of the plate 11 rather than a dogbone feature 34 as previously recited. The use of this embodiment remains the same in that the routing of the line 24 and the use of the first and second filaments 44, 46 remains may be used in any of the previously described methods.

Figure 19:
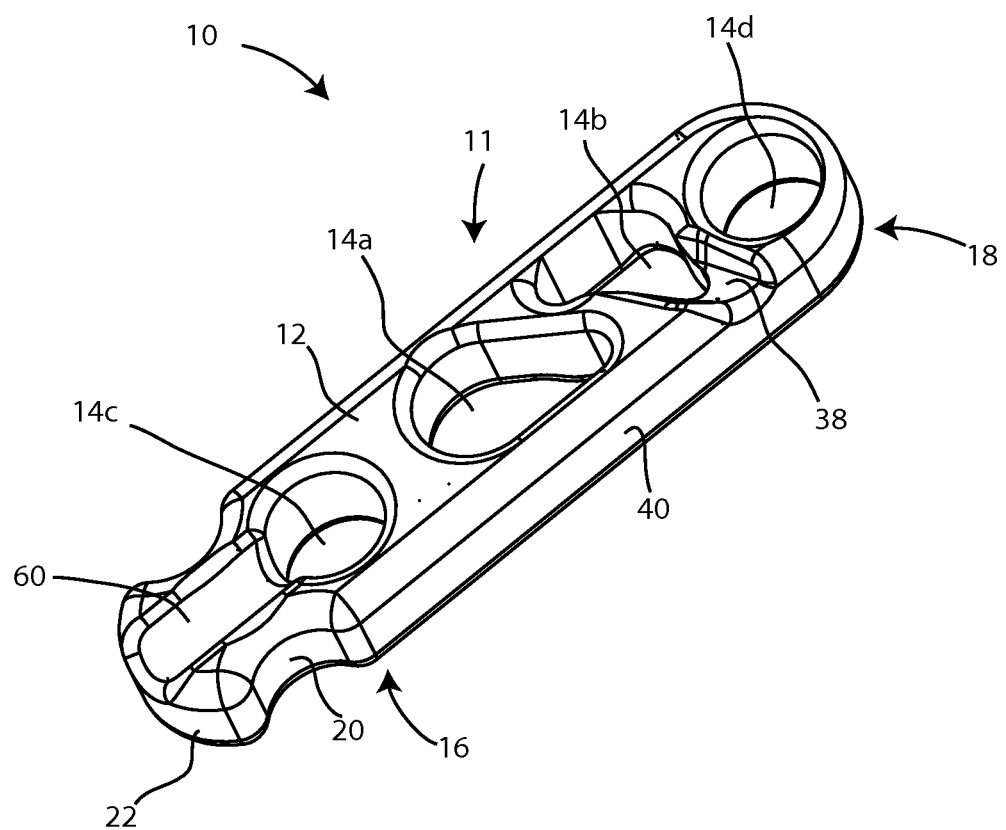
FIG. 19 illustrates a perspective view of an alternate embodiment of the plate of FIGS. 1-7, with the plate having a head, a neck and a body, the body with a plurality of passageways for receiving at least one line, and at least one deep groove extending from the end of the head to at least one of the plurality of passageways for receiving a line, without the line depicted.

Referring to FIG. 19, this alternate embodiment of the plate 11 may comprise features substantially similar to those already described herein. In this embodiment, however, the neck 20 and head 22 may comprise a deep groove 60 extending from one end of the head 20 to the first lateral passageway 14c. The deep groove 60 may provide easier passage of the first working portion 26 of the line 24 underneath the compression section 25.

Figure 20:
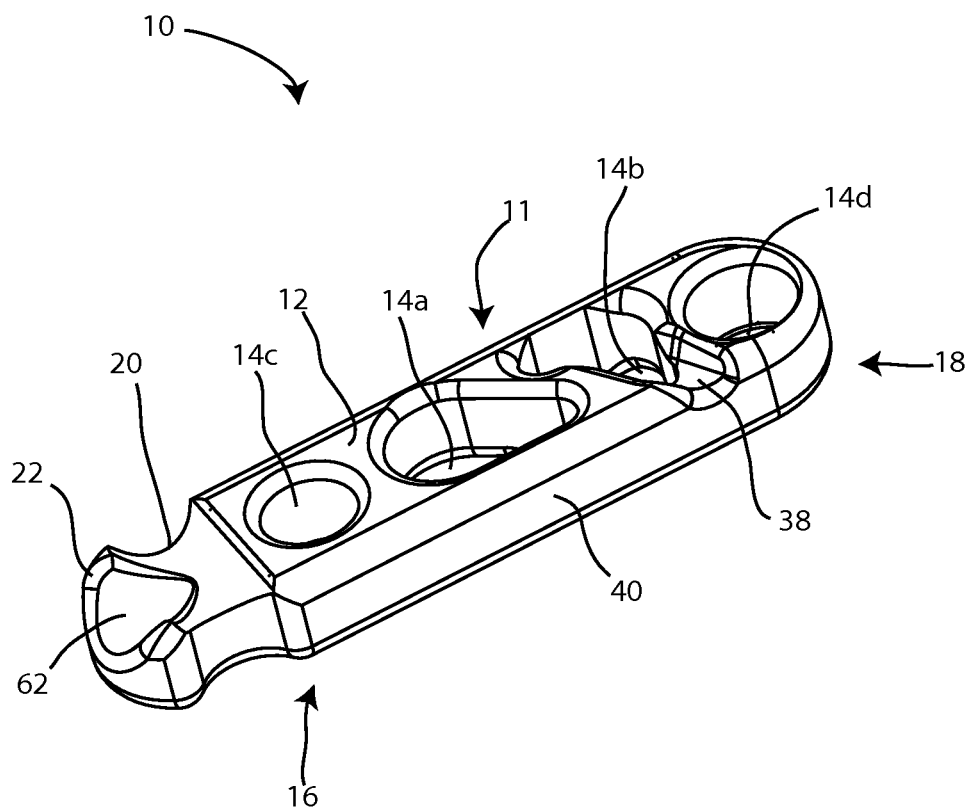
FIG. 20 illustrates a perspective view of an alternate embodiment of the plate of FIGS. 1-7, with the plate having a head, a neck and a body, the body with a plurality of passageways for receiving at least one line, and a cut out extending from the head toward the neck for receiving a line, without the line depicted.

Referring to FIG. 20, this alternate embodiment of the plate 11 may comprise features substantially similar to those already described herein. However, a cutout 62 may extend from the head 22 toward the neck 20. The cutout 62 may provide easier passage of the first working portion 26.

Other characteristics which are not depicted in FIGS. 1-20 may include other means of securing the second working portion of line in addition to the use of the compression section and routing of the lines to create a one-way slide. On the end opposite the dogbone feature of the plate a slot may extend from the opposite end into the body of the plate where in the slot gets wider as it moves further from the periphery of the plate. The slot may be configured to receive and pinch a line keeping the line substantially static after the appropriate length and tension of the line is determined. Other means for additional security may be the use of a cleat or locking feature extending from the plate opposite the dogbone feature. The cleat may be used to tie off the free end of the line after the appropriate length and tension of the line is determined.

Referring to FIGS. 21-27, examples of means for facilitating adjustment of line locks will now be described. Certain examples provide means for stabilizing the line lock while the line is adjusted, while other examples provide means for facilitating the adjustment of the line.

In particular, the disclosed examples may be suited to intraoperative or in situ adjustment of a line lock used to secure an ACL graft in a bone tunnel, although the technology is adaptable to many other situations inside and outside the medical field. Intraoperative adjustment may take place at any time during the surgical procedure, for example on a back table before the line lock is implanted. In situ adjustment may take place during the process of implanting the line lock, or thereafter. In situ adjustment may take place during a revision surgery some time after initial implantation of the line lock. Certain examples may disclose tools or accessories to stabilize the line lock against a bone portion, such as a lateral cortex of a distal femur so that the line lock does not lift off in response to tension on the line tending to adjust the line relative to the line lock. Other examples may provide tools or accessories to selectively decrease the self-locking action of the line in the line lock, so that it is easier to draw the line through the line lock.

Figure 21:
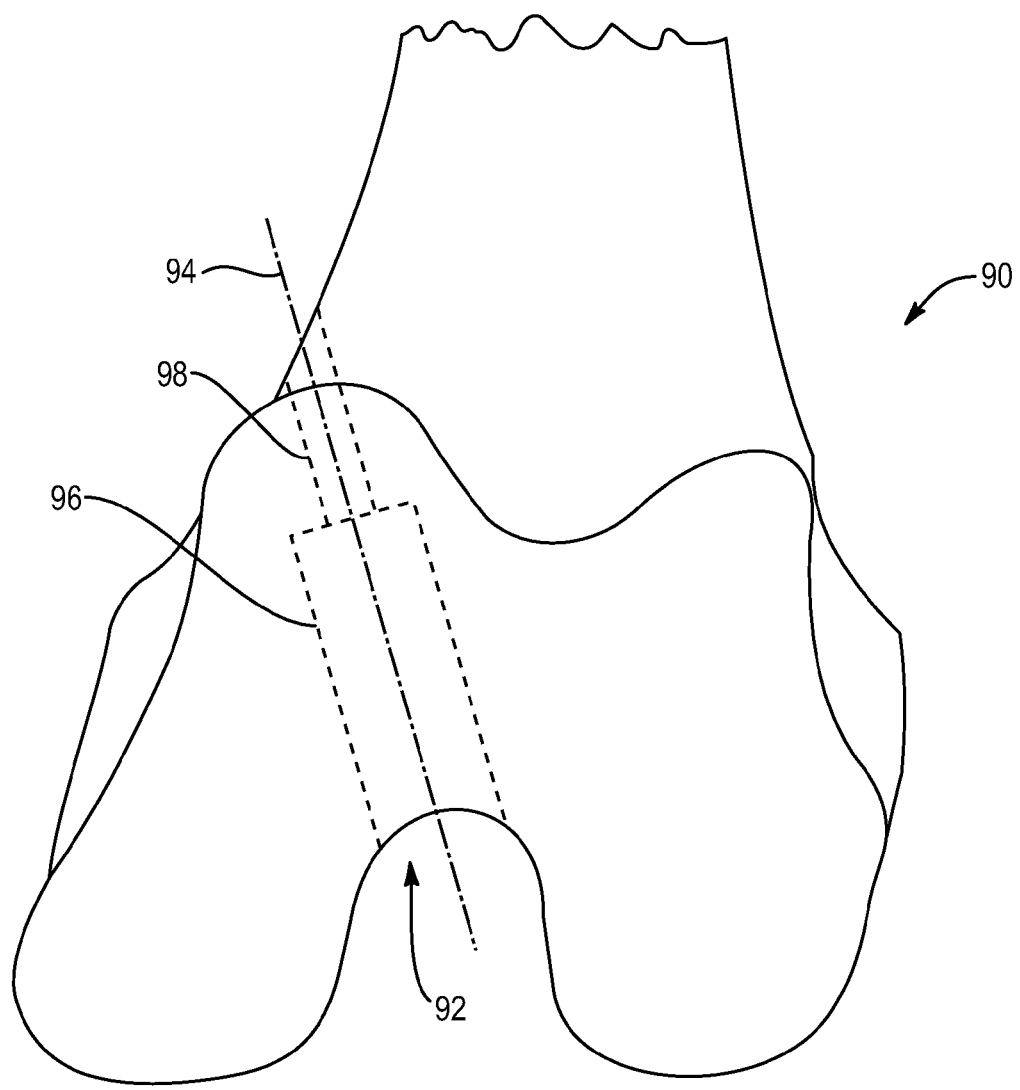
FIG. 21 is an anterior view of a distal femur with dashed lines showing a stepped bone tunnel in a lateral condyle of the femur.

Referring to FIG. 21, a distal portion of a femur 90 is shown from an anterior view. A bone tunnel 92 is shown in dashed lines. The bone tunnel 92 extends through a portion of the distal femur 90 along a central longitudinal axis 94. The bone tunnel 92 includes a first segment 96 and a second segment 98. The first segment 96 has a larger diameter than the second segment 98. Of course, the bone tunnel 92 may be a constant diameter over its entire length, or it may have more than the two segments shown. The bone tunnel 92 may also be a slot or groove, i.e., open along at least one side along its length. Although a femur with a bone tunnel is illustrated, any support structure may be envisioned instead. Furthermore, the support structure may be a hard structure, like a bone or other relatively rigid structure, or it may be a soft structure, like a ligament, tendon, fascia, muscle, or other resilient, compliant, flexible, or elastomeric structure.

Figure 22A:
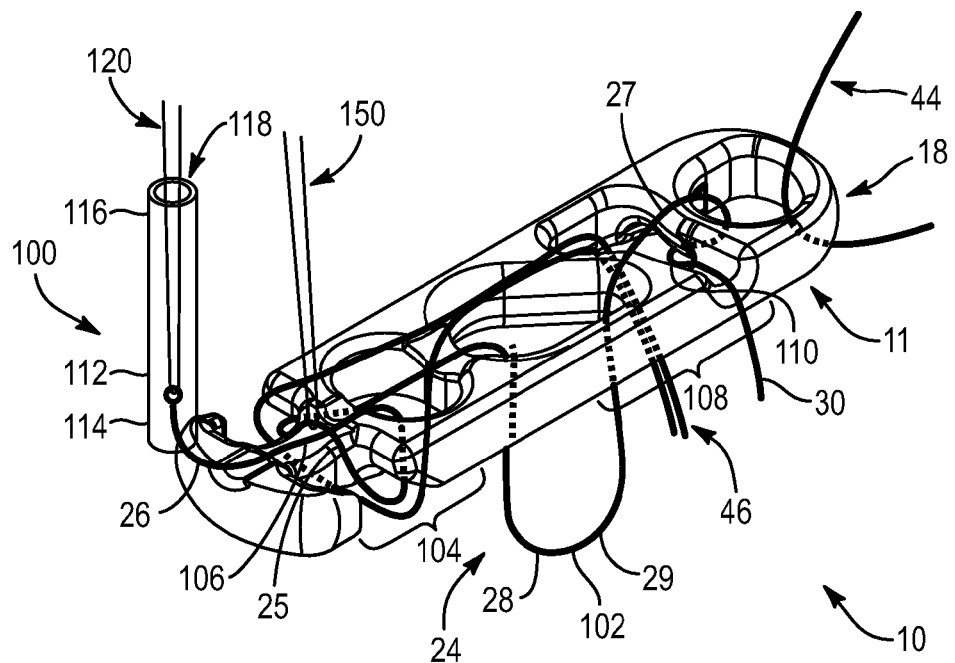
FIG. 22A is a perspective view of the plate, line, primary filament, and secondary filament of FIG. 1 with a line lock stabilizer and a compression limiter.

Referring to FIG. 22A, the plate 11, line 24, first filament 44, and second filament 46 of fixation device 10 of FIG. 1 are shown with a line lock stabilizer 100 and a compression limiter 150. The line 24 may be routed through the passageways 14 of the plate 11 to create a self-locking slide as in FIG. 1. Fixation device 10 or plate 11 may also be referred to as a line lock.

The portion of a line that is put under tension, typically to secure some object, is commonly referred to as a standing end, or standing portion. A standing portion may be secured to, or coupled to, an object as disclosed in U.S. Pat. Nos. 7,150,757; 7,566,339; 7,594,923; 7,641,694; 7,722,644; and U.S. patent application Ser. No. 11/142,933, all of which are incorporated herein by reference. The intermediate portion 28 of the line 24 may thus be described as a standing portion 102. The standing portion 102 is shown as a loop 29 connected at both ends to the plate 11, however, the standing portion 102 may extend straight instead, and may for example terminate in a free end. The portion of a line that extends toward a line handler is commonly referred to as a working end, or working portion, such as the first working portion 26 of the line 24.

A knot in a line, or a line lock attached to a line, is the demarcation between the standing portion and the working portion. The plate 11 attached to the line 24 is the demarcation between the standing portion 102 and the first working portion 26. The portion of the line 24 that is routed along the first pathway up through the passageway 14a, down through the passageway 14c, around the neck 20, up through the passageway 14c, and underneath the portion of the line 24 across the top of the neck 20 may be described as a first locking portion 104 of the line 24. The first locking portion 104 may include the first compression section 25 and a first compressed section 106. The first compression section 25 is the portion of the line 24 that extends around the neck 20. The first compressed section 106 is the portion of the line 24 which passes underneath the first compression section 25 and rests in the neck groove 32. The first compressed section 106 may also be referred to as a first constricted section 106 to differentiate it from the first compression section 25. It is appreciated that each of the portions 28, 102, 26, 104, 25, 106 of line 24 are relative to each other in that they change as line 24 is adjusted on line lock 10.

In the example shown, line 24 also includes a second working portion 30 which extends out of passageway 14b and a second locking portion 108 that extends between standing portion 102 and second working portion 30. The second locking portion 108 is the portion of the line 24 that is routed along the second pathway up through the passageway 14a, down through the passageway 14d, up through the passageway 14b, and underneath the portion of the line 24 extending between passageways 14a and 14d. The second locking portion 108 may include the second compression section 27 and a second constricted section 110. The second compression section 27 is the portion of the line 24 that extends between passageways 14a and 14d. The second constricted section 110 is the portion of the line 24 which passes underneath the second compression section 27 and rests in the periphery groove 38. It is appreciated that each of the portions 28, 102, 30, 108, 27, 110 of line 24 are relative to each other in that they change as line 24 is adjusted on line lock 10. Any description herein relating to the first working portion 26, the first locking portion 104, the first compression section 25, and/or the first constricted section 106 may be interpreted as though it refers to the second working portion 30, the second locking portion 108, the second compression section 27, and/or the second constricted section 110.

The line lock stabilizer 100 has a shaft 112 with a distal end 114 and an opposite proximal end 116. The distal end 114 may include means to engage the plate 11. For example, the distal end 114 may be flat, as shown, to engage a flat portion of the plate 11. The distal end 114 may include a projection, boss, tab, or key which engages a complementary recess in the plate 11, for example, one of the passageways 14, the neck opening 56, or a keyhole. Conversely, the distal end 114 may include a recess which engages a complementary protrusion, boss, tab, or key on the plate 11, for example, the neck 20, head 22, dogbone feature 34, or flange(s) 42. More than one protrusion/recess pair may be provided. The plate engagement means may also be threads, quick connect, bayonet fitting, snap fit, taper fit, friction fit, collet, hook, magnetic, electromagnetic, or the like. The proximal end 116 may include a grip or handle, and may include a retaining feature, such as a cleat or a slit. The shaft 112 may include a hole 118, which may be centrally or eccentrically located relative to an exterior surface of the shaft. Another type of longitudinal passageway such as a slot or groove may be provided instead of the hole 118, or such a passageway may be absent.

The line lock stabilizer 100 may be coupled to the plate 11 by engaging the complementary features on the distal end 114 and plate 11. The line lock stabilizer 100 may also be coupled to the plate 11 by securing a portion of the first filament 44 and/or second filament 46 to the retaining feature. For example, the filament 44 or 46 may be pulled taut and wrapped around a cleat or wedged into a slit. The filament 44 or 46 may pass alongside the shaft 112 or through the hole 118. A portion of the line 24, such as working portion 26, may pass alongside the shaft 112 or through the hole 118. Another filament 120 may be coupled to the working portion 26, as shown, and may pass alongside the shaft 112 or through the hole 118.

The line lock stabilizer 100 may be used to stabilize the line lock 10 while the length of the standing portion 102 is adjusted. The line lock stabilizer 100 resists tension in the line 24 tending to adjust the length of the standing portion 102. The line lock stabilizer 100 may be described as a counter-tension tool. The line lock stabilizer 100 may be used to push the line lock 10 against a support while the first working portion 26 is pulled to draw unwanted slack through the line lock 10.

Figure 22B:
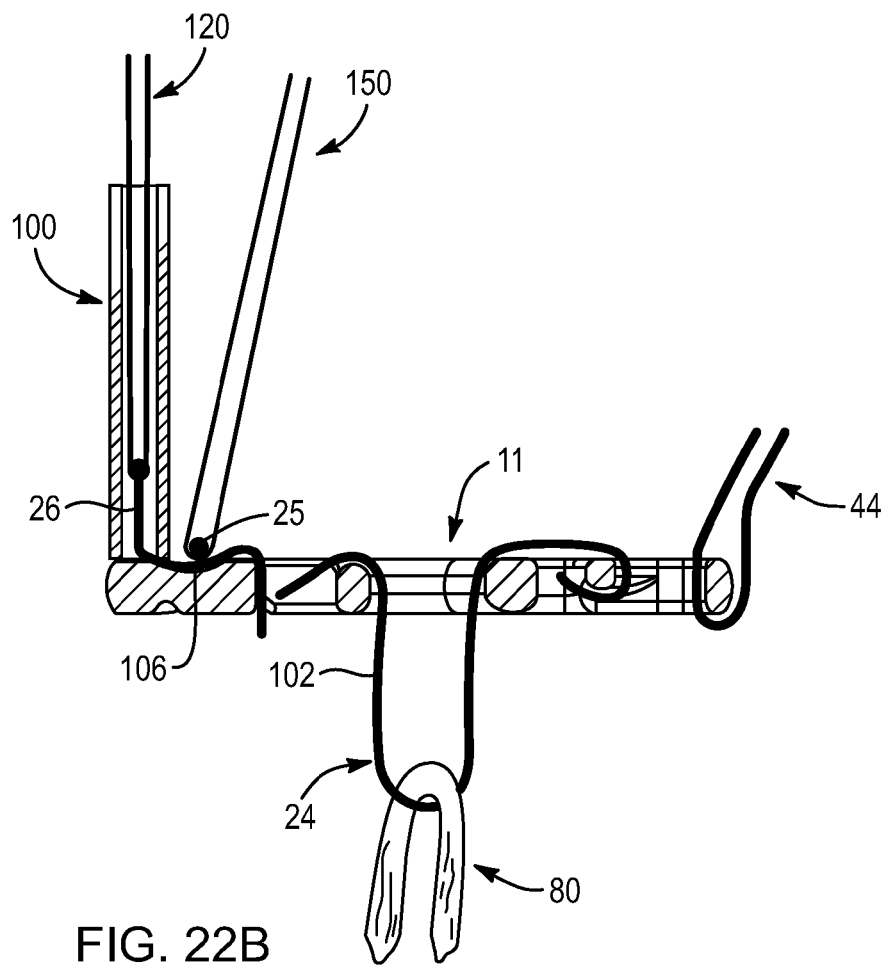
FIG. 22B is a side cross sectional view of the plate, line, primary filament, secondary filament, line lock stabilizer, and compression limiter of FIG. 22A with a graft.

Referring to FIGS. 21 and 22A-22B, an object such as an ACL graft 80 may be folded over the standing portion 102. The first filament 44 may be used to pull the plate 11, end 18 first, through the bone tunnel 92 so that the plate 11 exits the second segment 98 laterally, the standing portion 102 extends through the second segment 98 into the first segment 96, the folded portion of the ACL graft 80 is in the first segment 96, and the second filament 46 extends through the second segment 98 and the first segment 96. The first filament 44 extends laterally beyond the plate 11. The free ends of the ACL graft and second filament 46 extend medially beyond the mouth of the first segment 96. Once the plate 11 clears the bone tunnel 92, the second filament 46 may be pulled to flip the plate 11 to rest congruently on the bone surface around the bone tunnel 92. The line lock stabilizer 100 may be advanced over the first filament 44 to position the distal end 114 near the plate 11. The distal end 114 may be engaged with the plate 11. The first working portion 26 may pass through the hole 118, and the first filament 44 and first working portion 26 may extend from the proximal end 116 of the line lock stabilizer 100. The line lock stabilizer 100 may be used to push the plate 11 against the bone surface while the first working portion 26 is pulled to draw the line 24 through the plate 11 to adjust the length of the standing portion 102. If desired, the second working portion 30 may also pass through the hole 118 and extend from the proximal end 116 of the line lock stabilizer 100. The line lock stabilizer 100 may be used to push the plate 11 against the bone surface while the second working portion 30 is pulled to draw the line 24 through the plate 11 to adjust the length of the standing portion 102. The first and second working portions 26, 30 may be pulled independently, alternately, or simultaneously.

The compression limiter 150 may be a filament looped under the first compression section 25 before the plate 11 is pulled through the bone tunnel 92. Pulling on the compression limiter 150 may lift the first compression section 25 away from the first constricted section 106 and the plate 11 to reduce compression on the first constricted section 106. The compression limiter 150 alone may reduce compression on the first constricted section 106 enough that the line 24 is easily drawn through the plate 11 in either direction to adjust the length of the standing portion 102 shorter or longer. As soon as tension on the compression limiter 150 is released, the first compression section 25 is free to press the first constricted section 106 against the plate 11 in response to tension on the standing portion 102, so as to lock the line 24 to the plate 11. The compression limiter 150 may also be used in conjunction with the line lock stabilizer 100. In this arrangement, the compression limiter 150 may pass through the hole 118 and extend from the proximal end 116 of the line lock stabilizer 100.

The compression limiter 150 may extend between the plate 11 and the first compression section 25, between the plate 11 and the first constricted section 106, or between the first compression section 25 and the first constricted section 106. The compression limiter 150 may be coupled to the first compression section 25, the first constricted section 106, or the plate 11. The compression limiter 150 may be looped under the first compression section 25, the first constricted section 106, or both. Depending on these variables, the compression limiter 150 may separate or pull apart the plate 11 and the first compression section 25, the plate 11 and the first constricted section 106, or the first compression section 25 and the first constricted section 106.

Figure 23A:
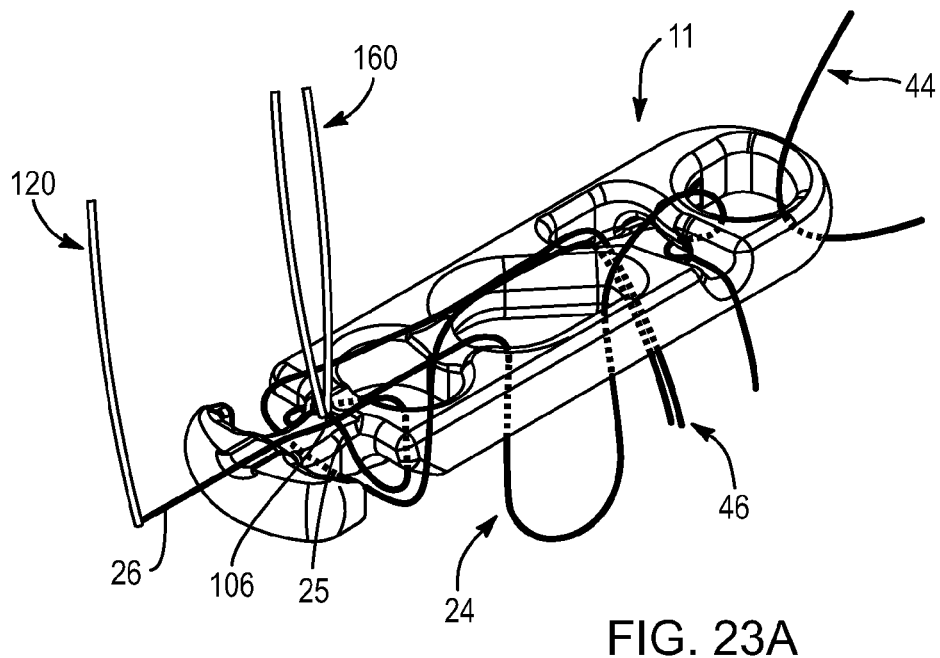
FIG. 23A is a perspective view of the plate, line, primary filament, and secondary filament of FIG. 1 with another compression limiter.
Figure 23B:
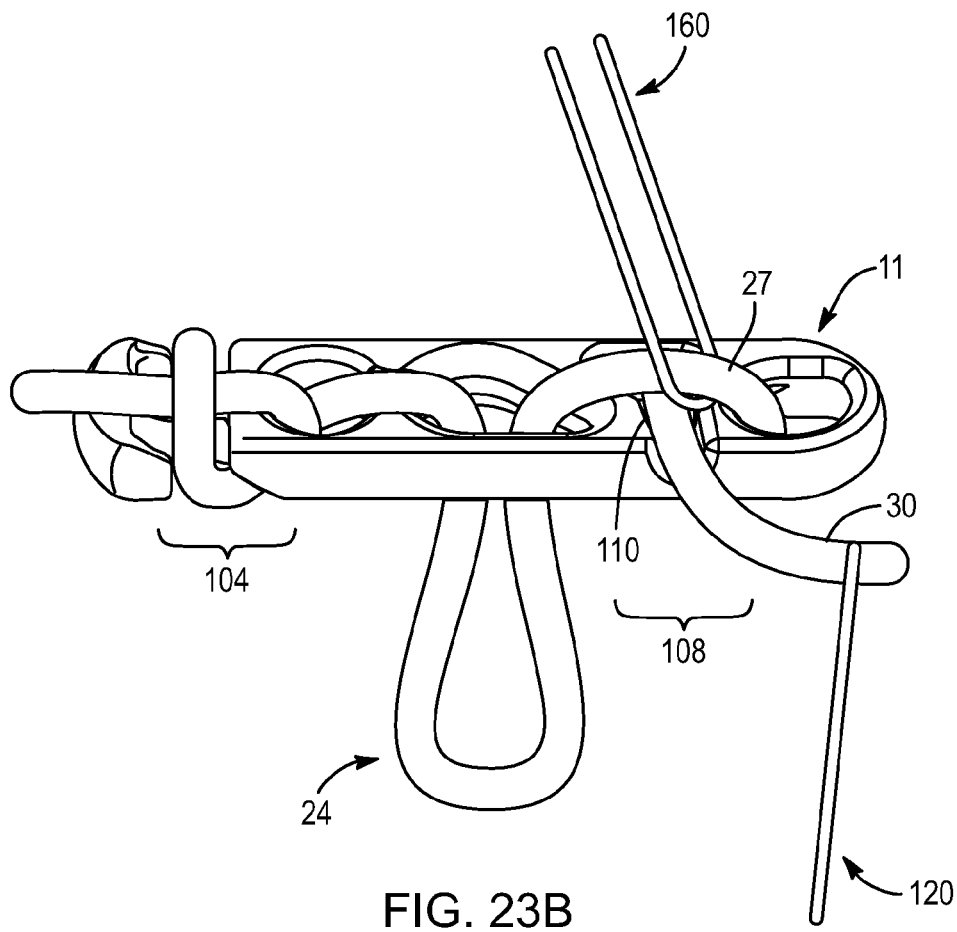
FIG. 23B is a side perspective view of the plate, line, and compression limiter of FIG. 23A.
Figure 23C:
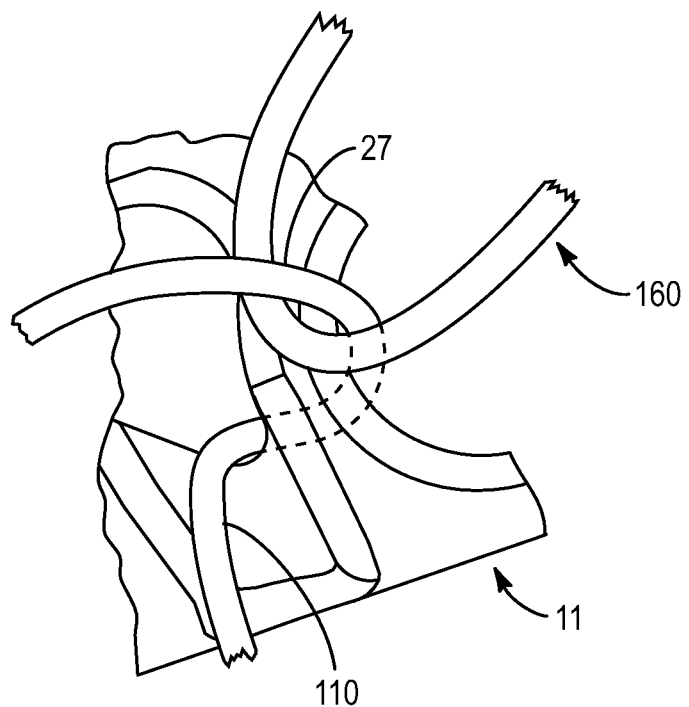
FIG. 23C is an enlarged detail view of a portion of the plate, line, and compression limiter of FIG. 23A.
Figure 23D:
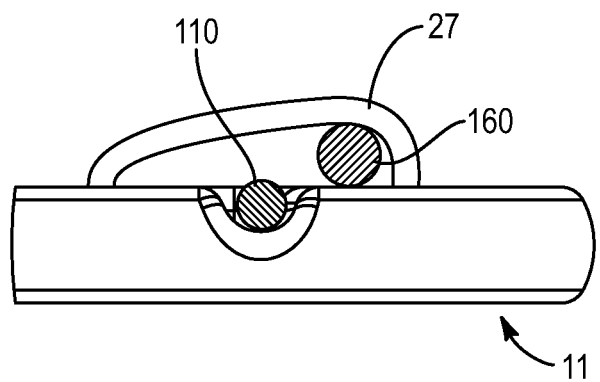
FIG. 23D is an enlarged detail view of the plate, line, and compression limiter of FIG. 23A with the line and compression limiter shown in cross-section.

Referring to FIG. 23A-D, the plate 11, line 24, first filament 44, and second filament 46 are shown with another compression limiter 160. In FIG. 23A, the compression limiter 160 is shown interacting with the first locking portion 104 and in FIGS. 23B-23D, the compression limiter 160 is shown interacting with the second locking portion 108. The compression limiter 160 may be a filament looped under the first compression section 25 before the plate 11 is pulled through the bone tunnel 92. The mere presence of the compression limiter 160 under the first compression section 25 may limit the amount of compression that the first compression section 25 can exert on the first constricted section 106, so that pulling on the compression limiter 160 is optional or unnecessary. For example, the compression limiter 160 may have a diameter large enough to hold the first compression section 25 spaced apart from the first constricted section 106. The diameter of the compression limiter 160 may be larger than the diameter of the line 24, at least where overlap exists, as illustrated in FIG. 23D, in which the constricted section 110 and the compression limiter 160 are shown in cross section. The compression limiter 160 alone may reduce compression on the first constricted section 106 enough that the line 24 is easily drawn through the plate 11 in either direction to adjust the length of the standing portion 102 shorter or longer. As soon as the compression limiter 160 is removed, the first compression section 25 is free to press the first constricted section 106 against the plate 11 in response to tension on the standing portion 102, so as to lock the line 24 to the plate 11. The compression limiter 150 may also be used in conjunction with the line lock stabilizer 100. In this arrangement, the compression limiter 150 may pass through the hole 118 and extend from the proximal end 116 of the line lock stabilizer 100. The compression limiter 160 may be removed by pulling it from the proximal end 116 after the length of the standing portion 102 is properly adjusted.

Figure 24A:
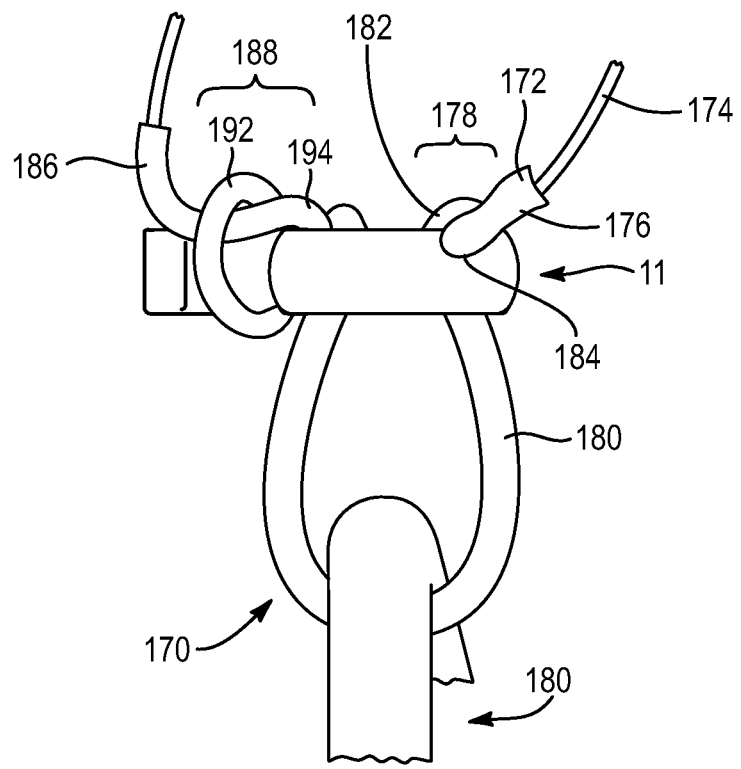
FIG. 24A is a side view of the plate of FIG. 1 with another line routed through the plurality of passageways, a loop of the line looped around a graft.
Figure 24B:
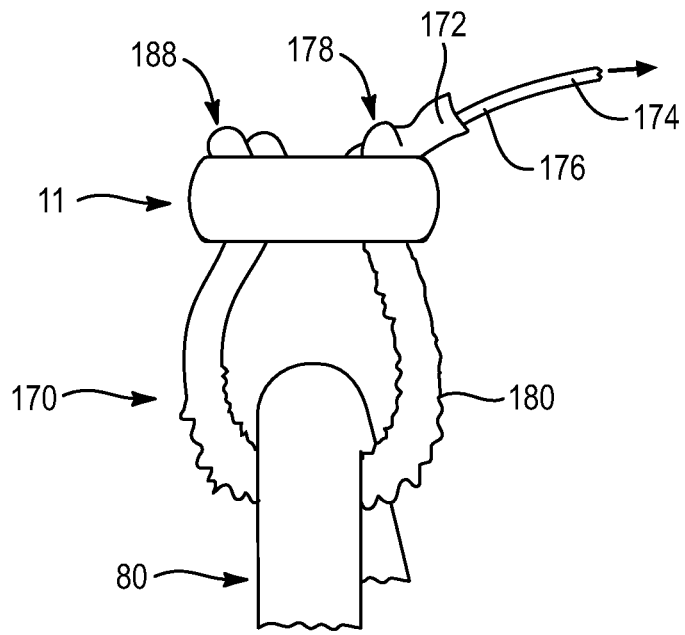
FIG. 24B is a side view of the plate and line of FIG. 24A, the loop adjusted to remove some slack around the graft.

Referring to FIGS. 24A-24B, the plate 11 and graft 80 are shown with a different line 170. Line 170 may be routed through the passageways 14 of plate 11 as described above for line 24, or at least as described for the portion of line 24 including the first working portion 26, the first locking portion 104, and the standing portion 102.

Line 170 includes an outer layer 172 and an inner portion 174. The outer layer 172 may be a braided or woven sheath, which may also be called a mantle. The inner portion 174 may be monofilament, multifilament, straight, twisted, braided, woven, or the like. The inner portion 174 may be slidably received in the outer layer 172. Line 170 may include a first working portion 176 like working portion 26, a first locking portion 178 like locking portion 104, and a standing portion 180 like standing portion 102. The first locking portion 178 may include a first compression section 182 like compression section 25 and a first constricted section 184 like constricted section 106. Line 170 may also include a second working portion 186 like working portion 30 and a second locking portion 188 like locking portion 108. The second locking portion 188 may include a second compression section 192 like compression section 27 and a second constricted section 194 like constricted section 110. The outer layer 172 may cover some or all of the inner portion 174. The outer layer 172 may be present in one or more of the portions 176, 178, 180, 182, 184, 186, 188, 192, and 194.

Line 170 may be drawn through the plate 11 to adjust the length of the standing portion 180 in a manner similar to that described in the preceding embodiments. The outer layer 172 and inner portion 174 may be pulled together through the plate 11. Alternatively, only the outer layer 172 or inner portion 174 may be pulled through the plate 11. For example, the inner portion 174 may be pulled through the plate 11, causing the outer layer 172 to bunch up. The outer layer 172 may be present in the constricted section 184, as shown. In another example, the outer layer 172 may be present in the standing portion 180 and absent in the constricted section 184. In yet another example, the free end of the working portion 176 may be fixed to the plate 11 or support.

Figure 25A:
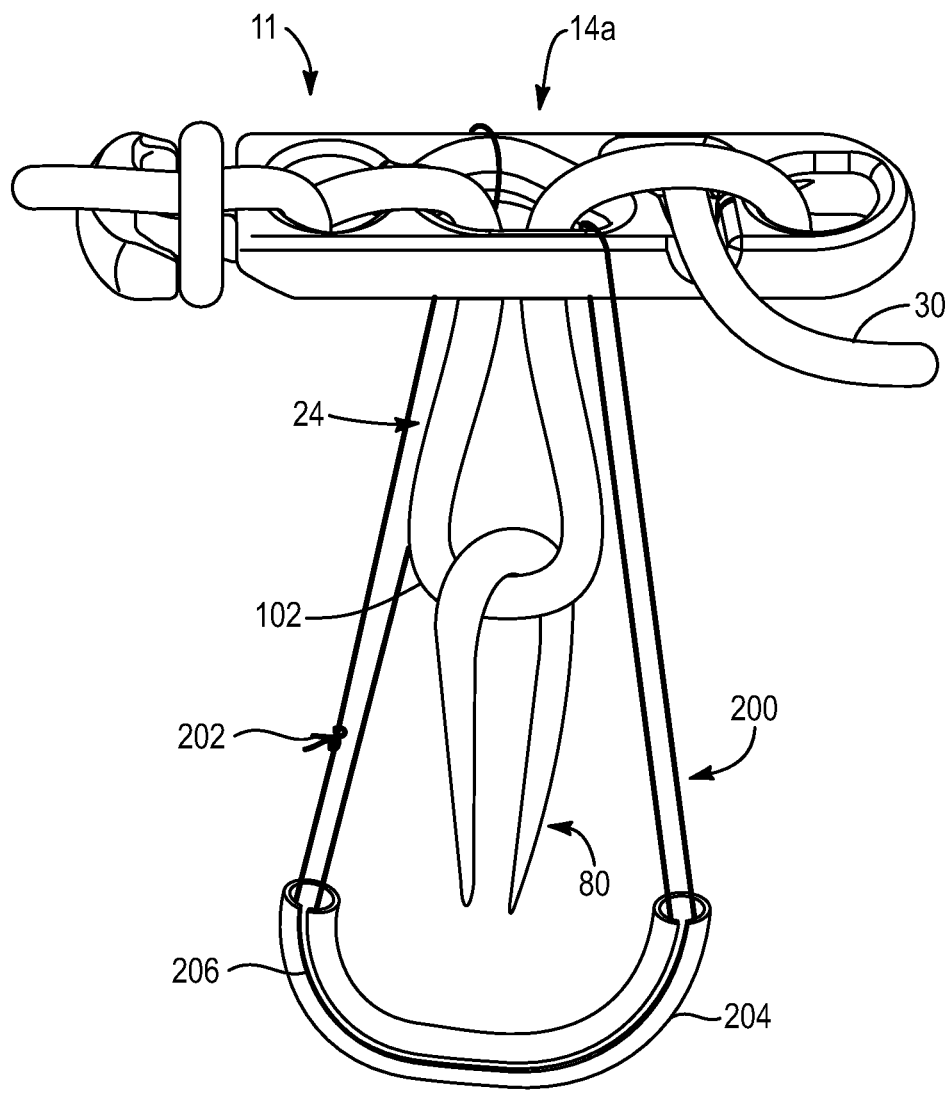
FIG. 25A is a side perspective view of the plate and line of FIG. 1 with a graft and another line lock stabilizer.
Figure 25B:
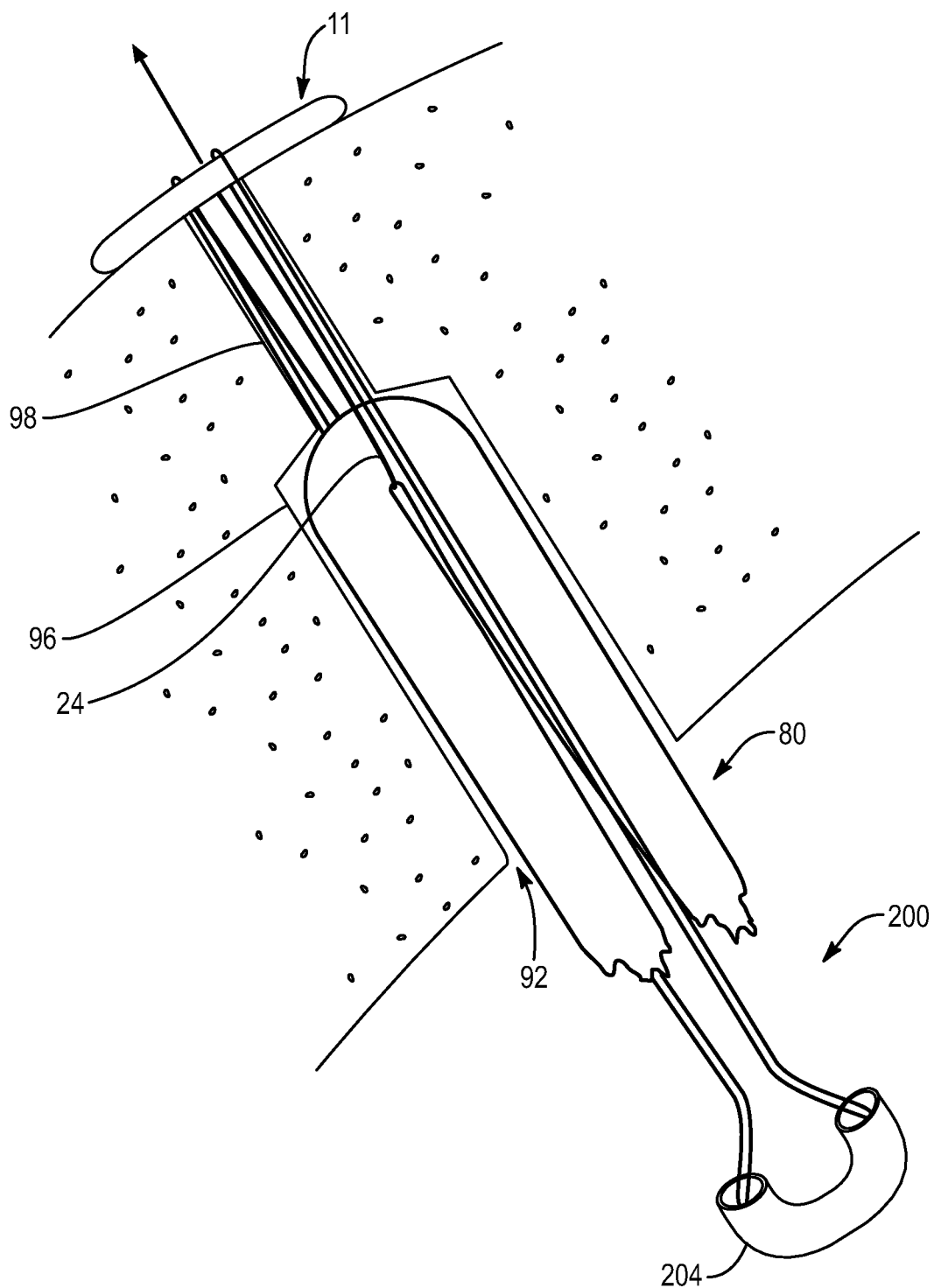
FIG. 25B is a cross section view of the plate, line, graft, and line lock stabilizer of FIG. 25A in the tunnel of FIG. 21.

Referring to FIGS. 25A-25B, the plate 11 and line 24 of fixation device 10 of FIG. 1 are shown with another line lock stabilizer 200 and the graft 80. The line 24 may be routed through the passageways 14 of the plate 11 to create a self-locking slide as in FIG. 1.

The line lock stabilizer 200 may be a filament routed through one or more of the passageways 14 of the plate 11. For example, the line lock stabilizer 200 may be a single strand formed into a continuous loop by a knot 202, splice, crimp, or other securing means. A portion of the line lock stabilizer 200 may be passed through the passageway 14a and an end 16 or 18 of the plate may be passed through a remainder of the line lock stabilizer 200 so that the line lock stabilizer 200 loops over the plate 11 on opposite sides of the passageway 14a as shown in FIG. 25A. The line lock stabilizer 200 may be said to be doubled over the plate 11. A handle 204 may be included with the line lock stabilizer 200. The handle 204 may rest over the doubled line lock stabilizer 200 and may be broader than the line lock stabilizer 200. The handle 204 may be a tube, and may have a slot 206 along its length so that the line lock stabilizer 200 may slide laterally in and out of the handle 204.

Referring to FIGS. 21 and 25B, the line lock stabilizer 200 may be doubled over the plate 11 before the plate 11, line 24, and graft 80 are passed through the tunnel 92. The line lock stabilizer 200 may be aligned with the standing portion 102 and the graft 80 before the first filament 44 is used to pull the plate 11 through the tunnel 92, as described previously so that the graft is in the first segment 96, the first working portion 26 extends laterally beyond the plate 11, and the free ends of the ACL graft and line lock stabilizer 200 extend medially beyond the mouth of the first segment 96. Once the plate 11 clears the bone tunnel 92, the plate 11 may be flipped to rest congruently on the bone surface around the bone tunnel 92. The plate 11 may be flipped by pulling on the second filament 46 or by pulling on the line lock stabilizer 200. The line lock stabilizer 200 may be used to pull the plate 11 against the bone surface or other support while the first working portion 26 is pulled to draw the line 24 through the plate 11 to adjust the length of the standing portion 102. If desired, the second working portion 30 may also extend laterally beyond the plate 11 alongside the first working portion 26. The line lock stabilizer 100 may be used to pull the plate 11 against the bone surface while the second working portion 30 is pulled to draw the line 24 through the plate 11 to adjust the length of the standing portion 102. The first and second working portions 26, 30 may be pulled independently, alternately, or simultaneously.

When the apparatus and methods of line lock stabilizer 200 are compared to those for line lock stabilizer 100, certain differences may be observed. Line lock stabilizer 200 acts through the bone tunnel 92 in the same way that tension on the graft 80 will act over the long term. The laterally-extending elements associated with line lock stabilizer 200 are all suture or filament structures, which may be much smaller in diameter than line lock stabilizer 100. Therefore, the use of line lock stabilizer 200 may result in a smaller lateral wound (i.e., scar).

In another example, a line lock stabilizer may be a single strand routed through passageway 14a of the plate 11 and beside the periphery 40 of the plate 11. In this example, the line lock stabilizer may be said to be folded over a portion of the plate 11. In this example, the free ends of the line lock stabilizer may be pulled simultaneously. Alternatively, the ends may be knotted or otherwise secured together, and an optional handle may be used to improve comfort while pulling on the line lock stabilizer.

The second filament 46 may also be used as a line lock stabilizer. As described above, the second filament 46 may be coupled to the plate 11 or line 24 and may remain in the bone tunnel 92 after the plate has been flipped or toggled to rest against the bone surface. Therefore, the second filament 46 may be used to pull the plate 11 down against a bone surface or other support.

Figure 26A:
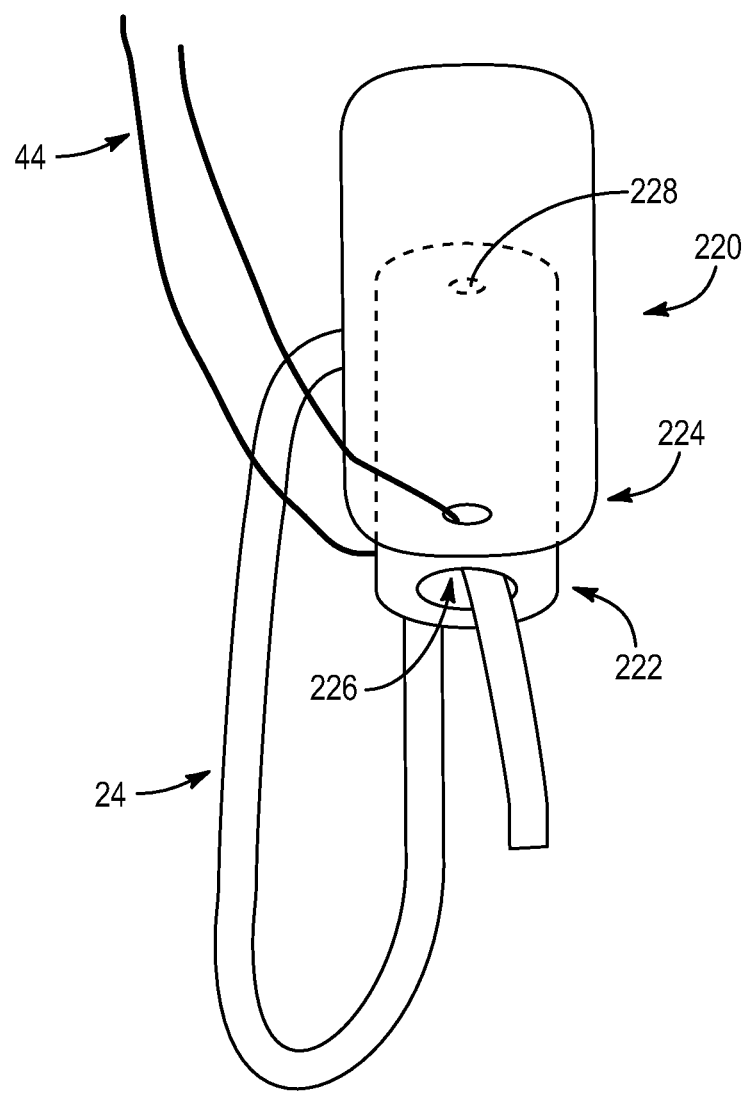
FIG. 26A is a side view of another line lock with a plate with a plurality of passageways and a member coupled to the plate, a line routed through the plurality of passageways, and a primary filament, the line lock in a first configuration.
Figure 26B:
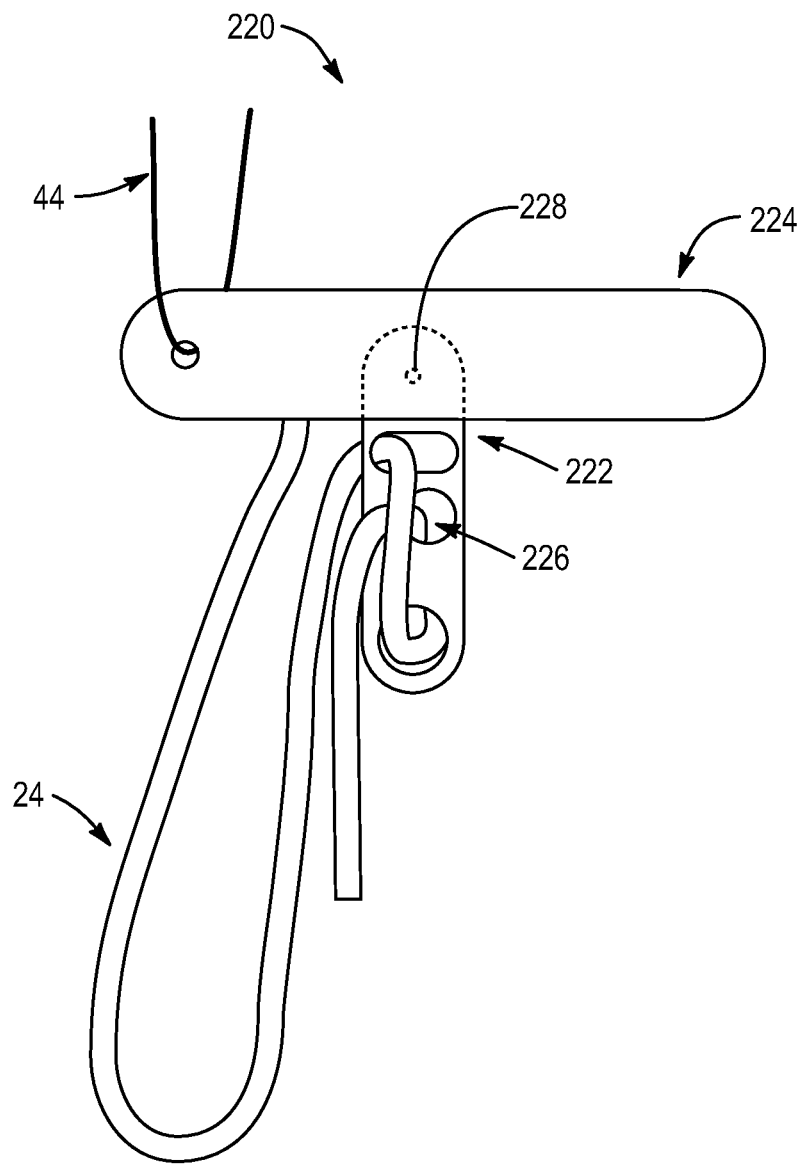
FIG. 26B is a front view of the line lock, line, and filament of FIG. 26A in a second configuration.

Referring to FIGS. 26A-26B, another line lock apparatus 220 is shown with the line 24 and the first filament 44. The line lock 220 may include a plate 222 and a toggle member 224.

The plate 222 may share some or all of the characteristics set forth for plate 11 or any of the other line locks disclosed herein. The plate 222 may include a plurality of passageways 226.

The toggle member 224 may be a generally elongated component, such as a generally rectangular or oval solid. The toggle member 224 may be another plate-like structure.

The toggle member 224 may be coupled to the plate 222. A coupling 228 may position the toggle member 224 transverse to the plate 222. The coupling 228 may permit the toggle member 224 to move relative to the plate 222 through a range of motion. The coupling 228 may be a hinge, a swivel, a joint, a pivot, a tether, a deformable element, or the like. The range of motion may include a position in which the toggle member 224 is transverse to the plate 222, and a position in which the toggle member 224 is aligned with the plate 222. The range of motion may also include a position in which the toggle member 224 is perpendicular to the plate 222, and a position in which the toggle member 224 is parallel to the plate 222.

Referring to FIG. 26B, the first working portion 26, first locking portion 104, and standing portion 102 of the line 24 may be routed through at least some of the passageways 226 of the plate 222 in the manner described above for plate 11 in FIG. 1. The second working portion 30 may be secured to the toggle member 224. In this arrangement, when the plate 222, toggle member 224, and line 24 are operatively assembled, the first working portion 26 and standing portion 102 may be said to extend from the same side of the toggle member 224. The plate 222, toggle member 224, and line 24 may also be said to extend from opposite sides of the plate 222. In another example, the second working portion 30, second locking portion 108 may be routed through at least some of the passageways 226 as an alternate to, or in combination with, the portions 26, 104, and 102.

Referring to FIGS. 21 and 26B, an object such as an ACL graft 80 may be folded over the standing portion 102. The first filament 44 may be used to pull the line lock 220, line 24, and graft 80 through the bone tunnel 92 so that the toggle member 224 exits the second segment 98, the standing portion 102 extends through the second segment 98 into the first segment 96, the folded portion of the ACL graft 80 is in the first segment 96, and the first working portion 26 extends medially beyond the mouth of the first segment 96. The line lock 220 may pass easily through the bone tunnel 92 when the toggle member 224 is aligned with the plate 222 and the line lock 220 is passed lengthwise through the bone tunnel 92. Once the toggle member 224 clears the bone tunnel 92, the toggle member 224 may be flipped to rest congruently against the bone surface around the bone tunnel 92. The toggle member 224 may be said to be transverse to the bone tunnel 92. The plate 222 remains in the bone tunnel 92. The line lock 220 may be said to expand as the toggle member 224 moves from an aligned position to a transverse position relative to the plate 222. In this example, the line lock 220 may be automatically stabilized against the bone surface when the first working portion 26 is pulled through the bone tunnel 92 to draw the line 24 through the plate 222 to adjust the length of the standing portion 102. The first working portion 26 may be said to act as a line lock stabilizer in this arrangement. The first working portion 26 is aligned with the standing portion 102 because both extend through the bone tunnel 92. Therefore, tension on the first working portion 26 is aligned with tension on the standing portion 102 by the graft 80.

Figure 27:
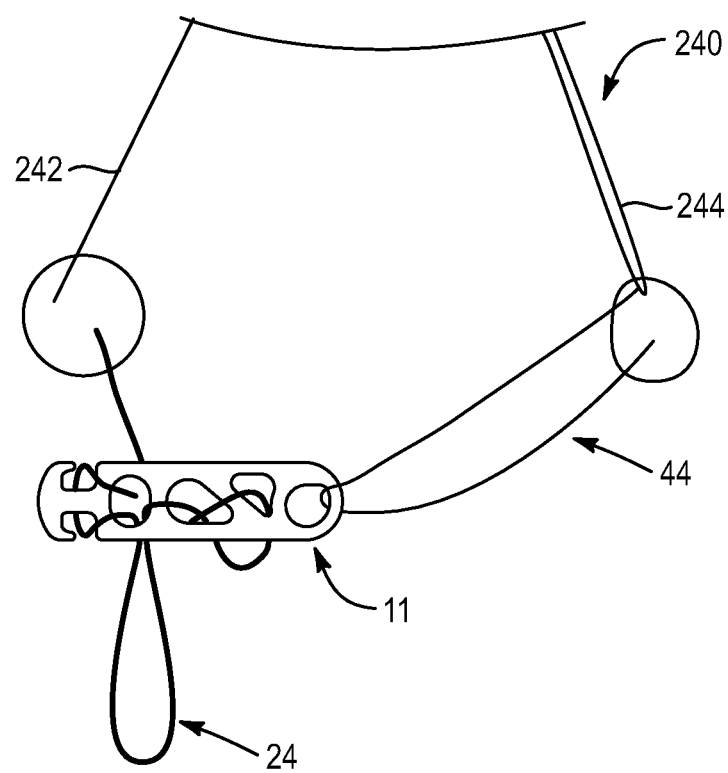
FIG. 27 is a perspective view of the plate, line, and primary filament of FIG. 1 with a line lock tensioning tool.

Referring to FIG. 27, the plate 11, line 24, and first filament 44 are shown with a line lock tensioner 240. The tensioner 240 may provide one or more of the functions of stabilizing the plate 11, reducing compression on the constricted section, or applying tension to draw the line 24 through the plate 11.

The tensioner 240 may include a pair of opposing arms 242, 244 movably coupled together. The arms 242, 244 may open and close along a linear or angular path. FIG. 27 shows arms 242, 244 movably coupled together to open and close along an angular path. In one example, the arms 242, 244 may be coupled together by an arcuate rail sliding in an arcuate slot of complementary shape, such as dovetail or T-shape. A ratchet, gear, or motor may be provided in some examples.

The first arm 242 may couple to the first working portion 26 and the second arm 244 may couple to the first filament 44. For example, the arms 242, 244 may include locking jaws (not shown) within which the first working portion 26 and first filament 44 may be clamped. The arms 242, 244 may be close together, or closed, when initially coupled to the first working portion 26 and first filament 44. The arms 242, 244 may then be separated, or opened, to apply tension to the first working portion 26 to draw the line 24 through the plate 11, and counter tension to the first filament 44 to stabilize the plate 11. The tensioner 240 may pull the first working portion 26 and first filament 44 at oblique angles to the plate 11, or parallel to the plate 11. This arrangement may overcome at least some of the resistance provided by the tortuous pathway of the line 24 through the plate 11.

All of the embodiments illustrated and described herein may have features mixed and matched to create a plate of physician's choice. The plurality of passageways 14 may be spaced apart at greater or lesser distance from one another. Similarly the plurality of passageways 14 may reside nearer or further from the periphery 40 of the plate 11. Each of the plurality of passageways 14 may be smaller or larger so long as they are capable of receiving at least one line and/or filament.

The technology disclosed herein may be embodied in other specific forms without departing from its spirit or essential characteristics. For example, above are described various alternative examples of plates and securing of lines as well as routing of the line and the routing of filaments. It is appreciated that various features of the above-described examples can be mixed and matched to form a variety of other combinations and alternatives. It is also appreciated that this system is not limited to simply ACL repair and fixation. This system may also be used to secure other ligaments, tendons or soft or hard tissue. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system comprising:
    a line comprising a locking portion and a standing portion, wherein the locking portion comprises a constricted section and a compression section;
    a line lock comprising a body at least partially bounding a plurality of passageways; and
    a line lock stabilizer, wherein the line lock stabilizer is a shaft, wherein the shaft comprises a through hole;
    wherein the locking portion of the line is routed through at least some of the passageways so that the constricted section is between the line lock and the compression section and a length of the standing portion extends from the line lock;
    wherein the line lock stabilizer stabilizes the line lock while the length of the standing portion is adjusted.

2. The system of claim 1, wherein the standing portion couples the system to a structure.

3. The system of claim 2, wherein the standing portion is looped around the structure.

4. The system of claim 2, wherein the standing portion is embedded within the structure.

5. The system of claim 2, wherein the length of the standing portion is adjusted to remove slack between the line lock and the structure.

6. The system of claim 2, wherein the structure is selected from the group consisting of a soft tissue, a muscle, a cartilage, a cartilage graft, a fascia, a tendon, a ligament, a ligament graft, an anterior cruciate ligament graft, a hard tissue, a bone, an autograft, an allograft, a xenograft, and a synthetic graft.

7. The system of claim 1, wherein the line lock stabilizer resists tension in the line tending to adjust the length of the standing portion.

8. The system of claim 7, wherein the line lock stabilizer pushes on the line lock to resist tension in the line tending to adjust the length of the standing portion.

9. The system of claim 7, wherein the line lock stabilizer pulls on the line lock to resist tension in the line tending to adjust the length of the standing portion.

10. The system of claim 1, wherein the line lock stabilizer is coupled to the line lock.

11. The system of claim 10, comprising a key and keyhole connection between the line lock stabilizer and the line lock.

12. The system of claim 10, wherein the line lock stabilizer is routed through at least one of the passageways.

13. The system of claim 1, wherein the line lock stabilizer includes a filament.

14. The system of claim 1, wherein the constricted section is compressed between the compression section and the line lock in response to tension in the line tending to lengthen the standing portion so that the system resists lengthening of the standing portion.

15. The system of claim 1, wherein the line comprises a working portion, wherein the locking portion is between the working portion and the standing portion, wherein the length of the standing portion is adjusted by pulling on the working portion.

16. The system of claim 1, wherein the line comprises a second locking portion, wherein the standing portion is between the locking portion and the second locking portion, wherein the second locking portion is coupled to the line lock.

17. The system of claim 16, wherein the second locking portion comprises a second constricted section and a second compression section; wherein the second locking portion is routed through at least some of the passageways so that the second constricted section is between the line lock and the second compression section.

18. The system of claim 17, wherein the line comprises a first working portion and a second working portion, wherein the locking portion is between the first working portion and the standing portion, wherein the second locking portion is between the second working portion and the standing portion, wherein the length of the standing portion is adjusted by pulling on at least one of the first and second working portions.

19. A system comprising:
a line comprising a locking portion and a standing portion, wherein the locking portion comprises a constricted section and a compression section;
a line lock comprising a body at least partially bounding a plurality of passageways; and
a counter-tension tool;
wherein the locking portion of the line is routed through at least some of the passageways so that the constricted section is between the line lock and the compression section and a length of the standing portion extends from the line lock;
wherein the counter-tension tool stabilizes the line lock against tension in the line tending to draw the line through the line lock, wherein the counter-tension tool pulls the line lock against a support;
wherein the counter-tension tool is a shaft; and
wherein the shaft comprises a through hole.

20. A system comprising:
a line comprising a locking portion and a standing portion, wherein the locking portion comprises a constricted section and a compression section;
a line lock comprising a body at least partially bounding a plurality of passageways; and
a counter-tension tool;
wherein the locking portion of the line is routed through at least some of the passageways so that the constricted section is between the line lock and the compression section and a length of the standing portion extends from the line lock;
wherein the counter-tension tool stabilizes the line lock against tension in the line tending to draw the line through the line lock, wherein the counter-tension tool pulls the line lock against a support; and
wherein the line comprises a working portion, wherein the locking portion is between the working portion and the standing portion, wherein the line is drawn through the line lock by pulling on the working portion.

21. A system comprising:
a line comprising a locking portion and a standing portion, wherein the locking portion comprises a constricted section and a compression section;
a line lock comprising a body at least partially bounding a plurality of passageways; and
a counter-tension tool;
wherein the locking portion of the line is routed through at least some of the passageways so that the constricted section is between the line lock and the compression section and a length of the standing portion extends from the line lock;
wherein the counter-tension tool stabilizes the line lock against tension in the line tending to draw the line through the line lock, wherein the counter-tension tool pulls the line lock against a support; and
wherein the line comprises a second locking portion, wherein the standing portion is between the locking portion and the second locking portion, wherein the second locking portion is coupled to the line lock.

22. The system of claim 21, wherein the second locking portion comprises a second constricted section and a second compression section; wherein the second locking portion is routed through at least some of the passageways so that the second constricted section is between the line lock and the second compression section.

23. The system of claim 22, wherein the line comprises a first working portion and a second working portion, wherein the locking portion is between the first working portion and the standing portion, wherein the second locking portion is between the second working portion and the standing portion, wherein the line is drawn through the line lock by pulling on at least one of the first and second working portions.

24. A system comprising:
a line comprising a working portion, a locking portion, and a standing portion, wherein the locking portion is between the working portion and the standing portion, wherein the locking portion comprises a constricted section and a compression section; and
a line lock comprising a body at least partially bounding a plurality of passageways;
wherein the locking portion of the line is routed through at least some of the passageways so that the constricted section is between the line lock and the compression section, a length of the working portion extends from the line lock, and a length of the standing portion extends from the line lock;
wherein a tension on the line tending to lengthen the working portion is aligned with a tension on the line tending to lengthen the standing portion.

25. The system of claim 24, wherein the standing portion couples the system to a structure.

26. The system of claim 25, wherein the structure is selected from the group consisting of a soft tissue, a muscle, a cartilage, a cartilage graft, a fascia, a tendon, a ligament, a ligament graft, an anterior cruciate ligament graft, a hard tissue, a bone, an autograft, an allograft, a xenograft, and a synthetic graft.

27. The system of claim 24, wherein the working portion and the standing portion extend from opposite sides of the line lock.

28. The system of claim 24, wherein the working portion and the standing portion extend from the same side of the line lock.

29. The system of claim 24, wherein the line lock comprises a member coupled to the body, wherein the member is transverse to at least one of the tension tending to lengthen the working portion and the tension tending to lengthen the standing portion.

30. The system of claim 29, wherein the member is movable relative to at least one of the tension tending to lengthen the working portion and the tension tending to lengthen the standing portion, wherein a range of motion of the member relative to at least one of the tension tending to lengthen the working portion and the tension tending to lengthen the standing portion includes at least one transverse position in which the member is transverse to at least one of the tension tending to lengthen the working portion and the tension tending to lengthen the standing portion and at least one aligned position in which the member is aligned with at least one of the tension tending to lengthen the working portion and the tension tending to lengthen the standing portion.

31. The system of claim 29, wherein the member is movable relative to the body, wherein a range of motion of the member relative to the body includes at least one transverse position in which the member is transverse to the body and at least one aligned position in which the member is aligned with the body.

32. The system of claim 29, wherein the member pivots relative to the body.

33. A system comprising:
a line comprising a locking portion and a standing portion, wherein the locking portion comprises a constricted section and a compression section;
a line lock comprising a body at least partially bounding a plurality of passageways; and
a compression limiter;
wherein the locking portion of the line is routed through at least some of the passageways so that the constricted section is between the line lock and the compression section;
wherein the constricted section is compressed between the compression section and the line lock in response to tension in the line tending to draw the line along the routing along a first direction so that the system resists drawing the line along the first direction except when the compression limiter reduces compression on the constricted section to permit the line to be drawn along the pathway.

34. The system of claim 33, wherein the standing portion couples the system to a structure.

35. The system of claim 34, wherein the structure is selected from the group consisting of a soft tissue, a muscle, a cartilage, a cartilage graft, a fascia, a tendon, a ligament, a ligament graft, an anterior cruciate ligament graft, a hard tissue, a bone, an autograft, an allograft, a xenograft, and a synthetic graft.

36. The system of claim 33, wherein the compression limiter separates at least two items selected from the group consisting of the line lock, the compression section, and the constricted section.

37. The system of claim 33, wherein the compression limiter extends between at least two items selected from the group consisting of the line lock, the compression section, and the constricted section.

38. The system of claim 33, wherein the compression limiter is coupled to at least one item selected from the group consisting of the line lock, the compression section, and the constricted section.

39. The system of claim 33, wherein the compression limiter comprises a filament.

* * * * *